United States Patent
Lee et al.

(10) Patent No.: US 10,147,893 B2
(45) Date of Patent: Dec. 4, 2018

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Sunyoung Lee, Seoul (KR); Yoonhyun Kwak, Seoul (KR); Bumwoo Park, Seoul (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 273 days.

(21) Appl. No.: 15/093,400

(22) Filed: Apr. 7, 2016

(65) Prior Publication Data

US 2016/0301019 A1 Oct. 13, 2016

(30) Foreign Application Priority Data

Apr. 10, 2015 (KR) .................. 10-2015-0051134
Nov. 27, 2015 (KR) .................. 10-2015-0167514

(51) Int. Cl.
  *H01L 51/00* (2006.01)
  *C09K 11/06* (2006.01)
  (Continued)

(52) U.S. Cl.
  CPC ...... *H01L 51/0087* (2013.01); *C07F 15/0093* (2013.01); *C09K 11/025* (2013.01);
  (Continued)

(58) Field of Classification Search
  CPC .................. H01L 51/0087; C09K 2211/1062
  See application file for complete search history.

(56) References Cited

U.S. PATENT DOCUMENTS 4,605,475 A   8/1986 Roberts et al.
7,781,074 B2  8/2010 Sano et al.
(Continued)

FOREIGN PATENT DOCUMENTS

WO   1986-004363 A1   7/1986

OTHER PUBLICATIONS

Gang Cheng et al. "Structurally robust phosphorescent [Pt(ONCN)] emitters for high performance organic light-emitting devices with power efficiency up to 126 lm W-1 and external quantum efficiency over 20%", Chem. Sci. 2014, 5, 4819-4830.
(Continued)

*Primary Examiner* — Michael M Dollinger
(74) *Attorney, Agent, or Firm* — Cantor Colburn LLP

(57) ABSTRACT

An organometallic compound represented by Formula 1:

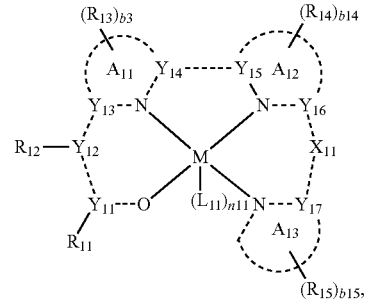

Formula 1 wherein, in Formula 1, M, $A_{11}$ to $A_{13}$, $L_{11}$, $R_{11}$ to $R_{15}$, $X_{11}$, $Y_{11}$ to $Y_{17}$, b13 to b15, and n11 are the same as described in the specification.

20 Claims, 1 Drawing Sheet

(51) Int. Cl.
　　　*C09K 11/02*　　　(2006.01)
　　　*C07F 15/00*　　　(2006.01)
　　　*H01L 51/50*　　　(2006.01)
(52) U.S. Cl.
　　　CPC .......... *C09K 11/06* (2013.01); *H01L 51/0072* (2013.01); *C09K 2211/1007* (2013.01); *C09K 2211/1011* (2013.01); *C09K 2211/1029* (2013.01); *C09K 2211/1044* (2013.01); *C09K 2211/185* (2013.01); *H01L 51/006* (2013.01); *H01L 51/5016* (2013.01)

(56) References Cited

U.S. PATENT DOCUMENTS

| | | | |
|---|---|---|---|
| 2009/0134384 A1* | 5/2009 | Stoessel | C07F 5/025 257/40 |
| 2013/0274473 A1 | 10/2013 | Che et al. | |
| 2015/0194616 A1* | 7/2015 | Li | H01L 51/0087 546/4 |
| 2016/0141515 A1* | 5/2016 | Hayama | C09K 11/06 257/40 |
| 2016/0293850 A1* | 10/2016 | Lee | H01L 51/0071 |

OTHER PUBLICATIONS

S. K. Huang et al. "The Analysis of Salen Complexes by Fast Atom Bombardment Mass Spectrometry and Atmospheric Pressure Chemical Ionization Mass Spectrometry", Journal of the American Society for Mass Spectrometry (1997), 8(9), 996-1009.

* cited by examiner

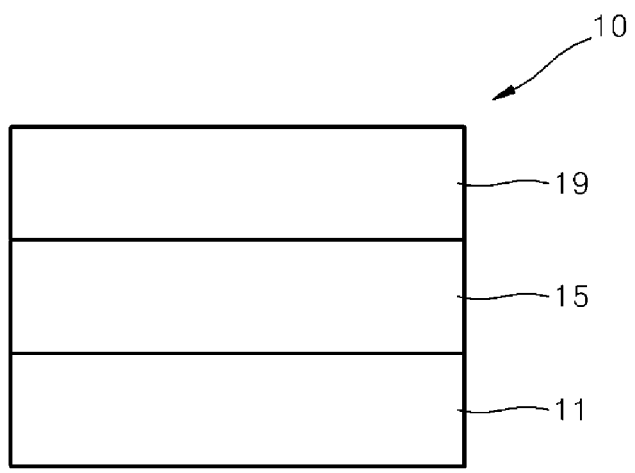

ORGANOMETALLIC COMPOUND AND ORGANIC LIGHT-EMITTING DEVICE INCLUDING THE SAME

CROSS-REFERENCE TO RELATED APPLICATIONS

This application claims priority to and the benefit of Korean Patent Application No. 10-2015-0167514, filed on Nov. 27, 2015, and Korean Patent Application No. 10-2015-0051134, filed on Apr. 10, 2015, in the Korean Intellectual Property Office, the contents of which are incorporated herein in their entirety by reference.

BACKGROUND

1. Field

One or more embodiments relate to an organometallic compound and an organic light-emitting device including the same.

2. Description of the Related Art

Organic light-emitting devices (OLEDs) are self-emission devices that have wide viewing angles, high contrast ratios, and short response times. In addition, OLEDs exhibit excellent brightness, driving voltage, and response speed characteristics, and produce full-color images.

A typical organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. The holes and the electrons, which are carriers, recombine in the emission layer to produce excitons. These excitons transition from an excited state to a ground state, thereby generating light.

Various types of organic light emitting devices are known. However, there still remains a need in OLEDs having low driving voltage, high efficiency, high brightness, and long lifespan.

SUMMARY

One or more embodiments include a novel organometallic compound and an organic light-emitting device including the same.

Additional aspects will be set forth in part in the description which follows and, in part, will be apparent from the description, or may be learned by practice of the presented embodiments.

According to one or more embodiments, an organometallic compound is represented by Formula 1:

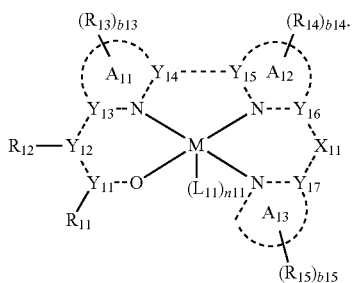

Formula 1

In Formula 1,

M may be selected from a Period I transition metal, a Period II transition metal, and a Period III transition metal, $A_{11}$ to $A_{13}$ may each independently be a $C_1$-$C_{20}$ heterocyclic group, $X_{11}$ may be selected from $C(R_{16})(R_{17})$ and $C(=O)$, $Y_{11}$ to $Y_{17}$ may each be a carbon atom, $Y_{11}$ and O, $Y_{11}$ and $Y_{12}$, $Y_{12}$ and $Y_{13}$, $Y_{13}$ and N, $Y_{14}$ and N, $Y_{14}$ and $Y_{15}$, $Y_{15}$ and N, $Y_{16}$ and N, $Y_{16}$ and $X_{11}$, $Y_{17}$ and $X_{11}$, and $Y_{17}$ and N may each independently be connected to each other via a single bond or a double bond, $R_{11}$ to $R_{17}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_3$-$C_{10}$ aryloxy group, a substituted or unsubstituted $C_1$-$C_{10}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), —B($Q_1$)($Q_2$), and —N($Q_1$)($Q_2$), wherein two neighboring groups selected from $R_{11}$ to $R_{17}$ may be optionally connected to each other to form a condensed ring, wherein $Q_1$ to $Q_3$ may each independently be selected from a $C_1$-$C_{60}$ alkyl group and a $C_6$-$C_{60}$ aryl group, b13 to b15 may each independently be selected from 1, 2, 3, 4, 5, 6, 7, 8, 9, and 10, $L_{11}$ may be selected from a monodentate ligand and a bidentate ligand, and n11 may be selected from 0, 1, and 2.

According to one or more embodiments, an organic light-emitting device includes:

a first electrode;

a second electrode; and an organic layer disposed between the first electrode and the second electrode, wherein the organic layer includes an emission layer and at least one organometallic compound represented by Formula 1.

The organometallic compound may be included in the emission layer. The emission layer may further include a host. The organometallic compound included in the emission layer may act as a dopant.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic cross-sectional diagram of a structure of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment may be represented by Formula 1:

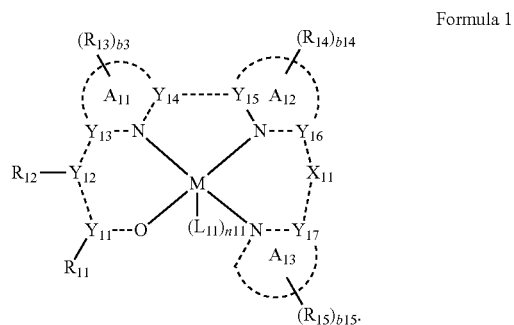

Formula 1

In Formula 1, M may be selected from a Period I transition metal, a Period II transition metal, and a Period III transition metal.

For example, in Formula 1, M may be selected from Period III transition metal, but is not limited thereto.

In various embodiments, in Formula 1, M may be selected from iridium (Ir), platinum (Pt), osmium (Os), gold (Au), hafnium (Hf), europium (Eu), terbium (Tb), and thulium (Tm), but is not limited thereto.

In various embodiments, in Formula 1, M may be selected from Os, Ir, and Pt, but is not limited thereto.

In various embodiments, in Formula 1, M may be Pt, but is not limited thereto.

$A_{11}$ to $A_{13}$ in Formula 1 may each independently be a $C_1$-$C_{20}$ heterocyclic group.

For example, $A_{11}$ to $A_{13}$ in Formula 1 may each independently be selected from a $C_1$-$C_{20}$ heterocycloalkane, a $C_1$-$C_{20}$ heterocycloalkene, and a $C_1$-$C_{20}$ heteroarene, but are not limited thereto.

In various embodiments, $A_{11}$ to $A_{13}$ in Formula 1 may each independently be selected from a pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, an isoindole, a benzimidazole, a benzoxazole, an isobenzoxazole, and an indazole, but are not limited thereto.

In various embodiments, $A_{11}$ to $A_{13}$ in Formula 1 may each independently be selected from a pyrrole, an imidazole, a pyrazole, a triazole, a pyridine, a pyrimidine, a pyrazine, a pyridazine, a triazine, a quinoline, an isoquinoline, an indole, an isoindole, a benzimidazole, and an indazole, but are not limited thereto.

In various embodiments, $A_{11}$ to $A_{13}$ in Formula 1 may each independently be selected from Formulae 2-1 to 2-6, but are not limited thereto:

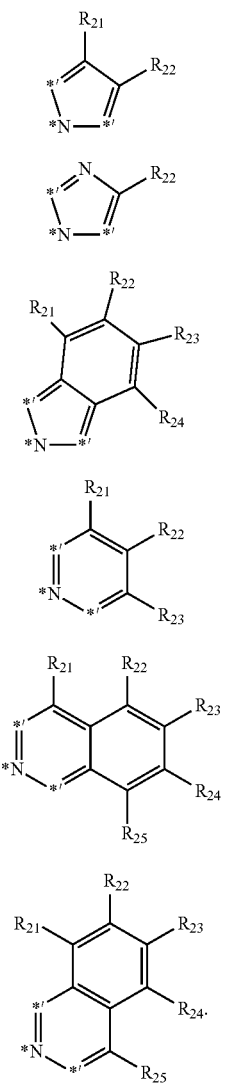

In Formulae 2-1 to 2-6,
* indicates a binding site to M in Formula 1,
*' indicates a binding site to a neighboring atom, and
$R_{21}$ to $R_{25}$ are each independently the same as described below in connection with $R_{11}$ in Formula 1.

$X_{11}$ in Formula 1 may be selected from $C(R_{16})(R_{17})$ and $C(=O)$, wherein $R_{16}$ and $R_{17}$ are the same as described below.

When $X_{11}$ in Formula 1 is $C(R_{18})(R_{17})$ and $R_{16}$ and $R_{17}$ are connected to each other to form a condensed ring, $X_{11}$ may be represented by one selected from Formulae 3-1 to 3-3, but is not limited thereto:

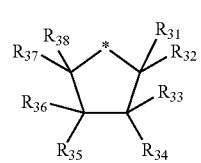

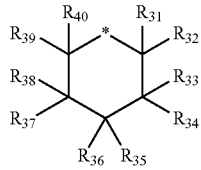

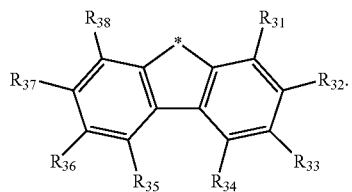

In Formulae 3-1 to 3-3,
* indicates a carbon atom of $X_{11}$ to which $R_{16}$ and $R_{17}$ are connected, and
$R_{31}$ to $R_{40}$ may each independently be selected from
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt there; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, $R_{31}$ to $R_{40}$ in Formulae 3-1 to 3-3 may each independently be selected from hydrogen, —F, a cyano group, a methyl group, an iso-propyl group, a tert-butyl group, and —$CF_3$, but are not limited thereto.

In various embodiments, $R_{31}$ to $R_{40}$ in Formulae 3-1 to 3-3 may be all hydrogen, but are not limited thereto.

$Y_{11}$ to $Y_{17}$ in Formula 1 may each be a carbon atom.
$Y_{11}$ and O, $Y_{11}$ and $Y_{12}$, $Y_{12}$ and $Y_{13}$, $Y_{13}$ and N, $Y_{14}$ and N, $Y_{14}$ and $Y_{15}$, $Y_{15}$ and N, $Y_{11}$ and N, $Y_{15}$ and $X_{11}$, $Y_{17}$ and $X_{11}$, and $Y_{17}$ and N in Formula 1 may each independently be connected to each other via a single bond or a double bond.

$R_{11}$ to $R_{17}$ in Formula 1 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), —B($Q_1$)($Q_2$), and —N($Q_1$)($Q_2$), wherein two neighboring groups selected from $R_{11}$ to $R_{17}$ may be optionally connected to each other to form a condensed ring, wherein $Q_1$ to $Q_3$ may each independently be selected from a $C_1$-$C_{60}$ alkyl group and a $C_6$-$C_{60}$ aryl group.

For example, $R_{11}$ to $R_{17}$ in Formula 1 may each independently be selected from hydrogen, deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, a tert-butoxy group, a phenyl group, —C(=O)($Q_1$), —Si($Q_1$)($Q_2$)($Q_3$), —B($Q_1$)($Q_2$), and —N($Q_1$)($Q_2$); and a phenyl group substituted with at least one selected from deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, and a tert-butoxy group, wherein $Q_1$ to $Q_3$ may each independently be selected from a methyl group, an ethyl group, an n-propyl group, an iso-propyl group, an n-butyl group, an iso-butyl group, a sec-butyl group, a tert-butyl group, and a phenyl group, but are not limited thereto.

In various embodiments, $R_{11}$ to $R_{17}$ in Formula 1 may each independently be selected from hydrogen, deuterium, —F, a cyano group, a methyl group, an ethyl group, an n-propyl group, an iso-propyl group, an n-butyl group, an iso-butyl group, a sec-butyl group, a tert-butyl group, —$CF_3$, —C(=O)($Q_1$), —Si($Q_1$)($Q_2$)($Q_3$), —B($Q_1$)($Q_2$), and —N($Q_1$)($Q_2$); and a phenyl group substituted with at least one selected from deuterium, —F, a cyano group, a methyl group, an ethyl group, an n-propyl group, an iso-propyl group, an n-butyl group, an iso-butyl group, a sec-butyl group, a tert-butyl group, and —$CF_3$, wherein $Q_1$ to $Q_3$ may each independently be selected from a methyl group, an ethyl group, an n-propyl group, an iso-propyl group, an n-butyl group, an iso-butyl group, a sec-butyl group, a tert-butyl group, and a phenyl group, but are not limited thereto.

In various embodiments, $R_{11}$ to $R_{17}$ in Formula 1 may each independently be selected from hydrogen, —F, a cyano group, a methyl group, an ethyl group, an iso-propyl group, a tert-butyl group, —$CF_3$, —Si($CH_3$)$_3$, and groups represented by Formulae 5-1 and 5-2, but are not limited thereto:

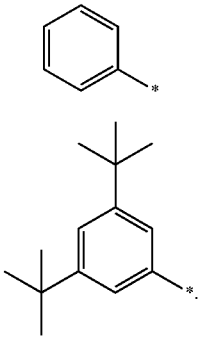

5-1

5-2

In Formulae 5-1 and 5-2,
* indicates a binding site to a neighboring atom.

For example, when two neighboring groups selected from $R_{11}$ to $R_{17}$ are connected to each other to form a condensed ring, the condensed ring may be further substituted with $R_{18}$, wherein the number of groups $R_{18}$ is represented by b18, and b18 may be selected from 1, 2, and 3; and groups $R_{18}$ may be identical to or different from each other.

$R_{18}$ in Formula 1 may be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), —B($Q_1$)($Q_2$), and —N($Q_1$)($Q_2$), wherein $Q_1$ to $Q_3$ may each independently be selected from a $C_1$-$C_{60}$ alkyl group and a $C_6$-$C_{60}$ aryl group.

For example, $R_{18}$ in Formula 1 may be selected from hydrogen, deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, a tert-butoxy group, a phenyl group, —C(=O)($Q_1$), —Si($Q_1$)($Q_2$)($Q_3$), —B($Q_1$)($Q_2$), and —N($Q_1$)($Q_2$); and a phenyl group substituted with at least one selected from deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, and a tert-butoxy group, wherein $Q_1$ to $Q_3$ may each independently be selected from a methyl group, an ethyl group, an n-propyl group, an iso-propyl group, an n-butyl group, an iso-butyl group, a sec-butyl group, a tert-butyl group, and a phenyl group, but are not limited thereto.

In various embodiments, $R_{18}$ in Formula 1 may be selected from hydrogen, deuterium, —F, a cyano group, a methyl group, an ethyl group, an n-propyl group, an iso-propyl group, an n-butyl group, an iso-butyl group, a sec-butyl group, a tert-butyl group, —CF$_3$, —C(=O)(Q$_1$), —Si(Q$_1$)(Q$_2$)(Q$_3$), —B(Q$_1$)(Q$_2$), and —N(Q$_1$)(Q$_2$); and a phenyl group substituted with at least one selected from deuterium, —F, a cyano group, a methyl group, an ethyl group, an n-propyl group, an iso-propyl group, an n-butyl group, an iso-butyl group, a sec-butyl group, a tert-butyl group, and —CF$_3$, wherein $Q_1$ to $Q_3$ may each independently be selected from a methyl group, an ethyl group, an n-propyl group, an iso-propyl group, an n-butyl group, an iso-butyl group, a sec-butyl group, a tert-butyl group, and a phenyl group, but are not limited thereto.

In various embodiments, $R_{18}$ in Formula 1 may be selected from hydrogen, —F, a cyano group, a methyl group, an ethyl group, an iso-propyl group, a tert-butyl group, —CF$_3$, —Si(CH$_3$)$_3$, and groups represented by Formulae 5-1 and 5-2, but is not limited thereto:

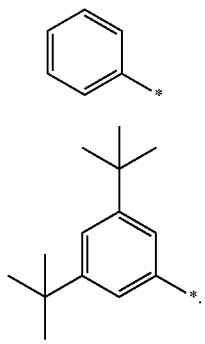

5-1

5-2

In Formulae 5-1 and 5-2,

* indicates a binding site to a neighboring atom.

b13 in Formula 1 indicates the number of groups $R_{13}$, wherein b13 may be selected from 1, 2, 3, 4, 5, 6, 7, 8, 9, and 10. For example, b13 may be selected from 1, 2, and 3 or may be 1, but is not limited thereto. When b13 is two or more, groups $R_{13}$ may be identical to or different from each other.

b14 in Formula 1 indicates the number of groups $R_{14}$, wherein b14 may be selected from 1, 2, 3, 4, 5, 6, 7, 8, 9, and 10. For example, b14 may be selected from 1, 2, and 3 or may be 1, but is not limited thereto. When b14 is two or more, groups $R_{14}$ may be identical to or different from each other.

b15 in Formula 1 indicates the number of groups $R_{15}$, wherein b15 may be selected from 1, 2, 3, 4, 5, 6, 7, 8, 9, and 10. For example, b15 may be selected from 1, 2, and 3 or may be 1, but is not limited thereto. When b15 is two or more, groups $R_{15}$ may be identical to or different from each other.

$L_{11}$ in Formula 1 may be selected from a monodentate ligand and a bidentate ligand.

For example, $L_{11}$ in Formula 1 may be selected from

I$^-$, Br$^-$, Cl$^-$, a sulfide, a nitrate, an azide, a hydroxide, a cyanate, an isocyanate, a thiocyanate, water, an acetonitrile, a pyridine, an ammonia, a carbon monoxide, PPh$_3$, PPh$_2$CH$_3$, PPh(CH$_3$)$_2$, and P(CH$_3$)$_3$; and an oxalate, an acetylacetonate, a picolinic acid, 1,2-bis(diphenylphosphino)ethane, 1,1-bis(diphenylphosphino)methane, a glycinate, and an ethylenediamine, but is not limited thereto.

In various embodiments, $L_{11}$ in Formula 1 may be selected from PPh$_3$, PPh$_2$CH$_3$, PPh(CH$_3$)$_2$, P(CH$_3$)$_3$, an oxalate, an acetylacetonate, and a picolinic acid, but is not limited thereto.

In various embodiments, $L_{11}$ in Formula 1 may be selected from PPh$_2$CH$_3$ and an acetylacetonate, but is not limited thereto.

n11 in Formula 1 indicates the number of groups $L_{11}$ and may be selected from 0, 1, and 2. For example, n11 may be zero, but is not limited thereto. When n11 is 2, two groups $L_{11}$ may be identical to or different from each other. When n11 is zero, it may mean that $L_1$ is not bonded to M.

In various embodiments, the organometallic compound represented by Formula 1 may be represented by one selected from Formulae 1-1 to 1-6:

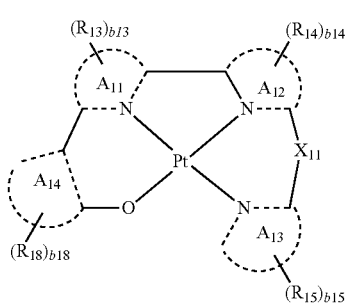

1-1

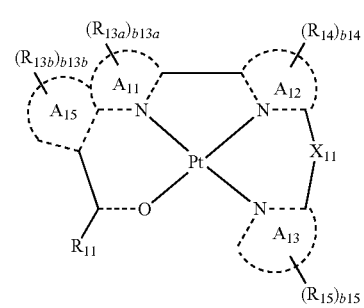

1-2

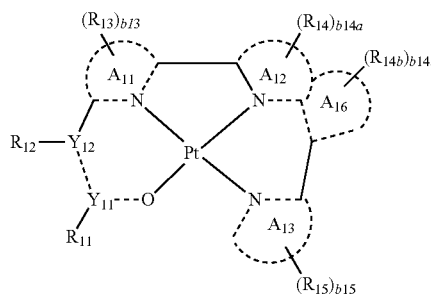

1-3

-continued

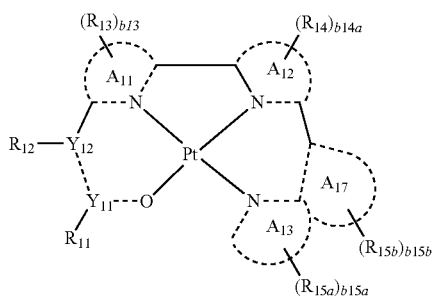

1-4

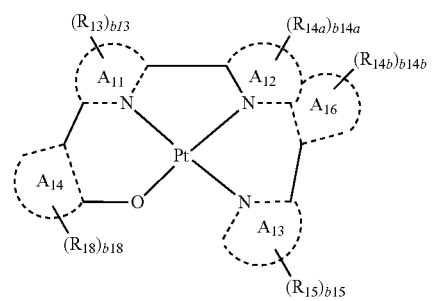

1-5

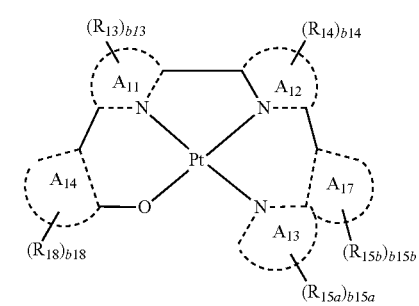

1-6

In Formulae 1-1 to 1-6, $A_{11}$ to $A_{13}$, $X_{11}$, $Y_{11}$, $Y_{12}$, $R_{11}$ to $R_{15}$, and b13 to b15 are the same as described above in connection with Formula 1, $R_{13a}$ and $R_{13b}$ are each independently the same as described above in connection with $R_{13}$ in Formula 1, $R_{14a}$ and $R_{14b}$ are each independently the same as described above in connection with $R_{14}$ in Formula 1, $R_{15a}$ and $R_{15b}$ are each independently the same as described above in connection with $R_{15}$ in Formula 1, $R_{18}$ is the same as described above in connection with $R_{11}$ in Formula 1, b13a and b13b are each independently the same as described above in connection with b13 in Formula 1, b14a and b14b are each independently the same as described above in connection with b14 in Formula 1, b15a and b15b are each independently the same as described above in connection with b15 in Formula 1, b18 is the same as described above in connection with b11 in Formula 1, and $A_{14}$ to $A_{17}$ may each independently be selected from a $C_5$-$C_{20}$ carbocyclic group and a $C_1$-$C_{20}$ heterocyclic group.

For example, $A_{14}$ to $A_{17}$ in Formulae 1-1 to 1-6 may each independently be selected from a $C_5$-$C_{20}$ cycloalkane, a $C_5$-$C_{20}$ cycloalkene, a $C_5$-$C_{20}$ arene, a $C_1$-$C_{20}$ heterocycloalkane, a $C_1$-$C_{20}$ heterocycloalkene, and a $C_1$-$C_{20}$ heteroarene, but are not limited thereto.

In various embodiments, $A_{14}$ to $A_{17}$ in Formulae 1-1 to 1-6 may each independently be selected from a benzene, a naphthalene, a fluorene, an indene, a furan, a thiophene, a carbazole, a benzofuran, a benzothiophene, a dibenzofuran, and a dibenzothiophene, but are not limited thereto.

In various embodiments, $A_{14}$ to $A_{17}$ in Formulae 1-1 to 1-6 may each independently be selected from a benzene and a naphthalene, but are not limited thereto.

In various embodiments, the organometallic compound represented by Formula 1 may be represented by one selected from Formulae 1-11 to 1-19 and 1-5, but is not limited thereto:

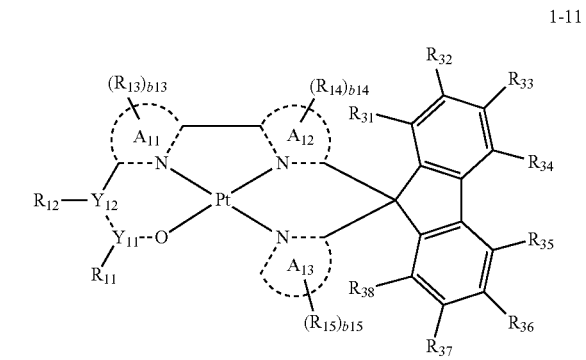

1-11

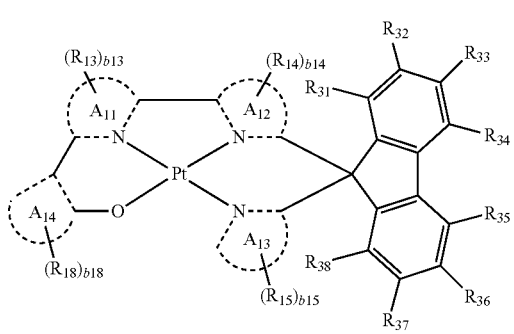

1-12

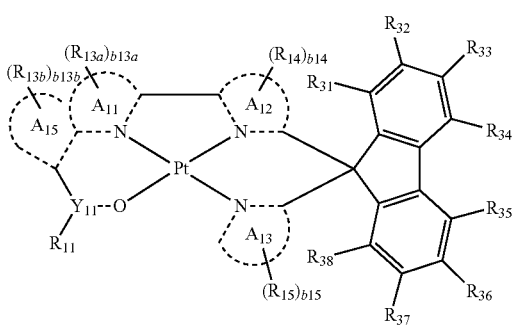

1-13

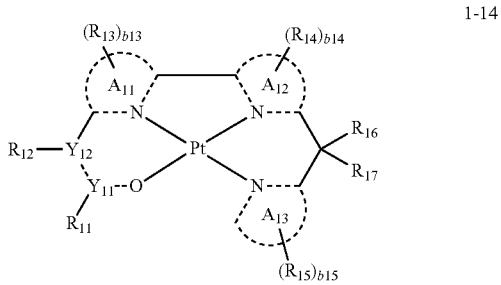

1-14

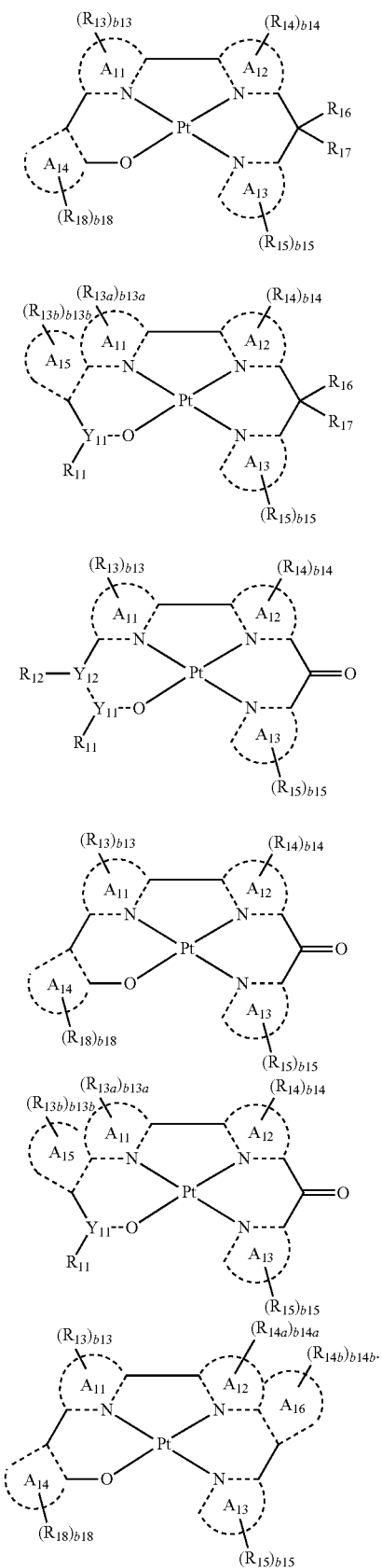

In Formulae 1-11 to 1-19 and 1-5, $A_{11}$ to $A_{13}$, $Y_{11}$, $Y_{12}$, $R_{11}$ to $R_{17}$, and b13 to b15 are the same as described above in connection with Formula 1, $R_{13a}$ and $R_{13b}$ are each independently the same as described above in connection with $R_{13}$ in Formula 1, $R_{14a}$ and $R_{14b}$ are each independently the same as described above in connection with $R_{14}$ in Formula 1, $R_{18}$ is the same as described above in connection with $R_{11}$ in Formula 1, b13a and b13b are each independently the same as described above in connection with b13 in Formula 1, b14a and b14b are each independently the same as described above in connection with b14 in Formula 1, b18 is the same as described above in connection with b11 in Formula 1, $A_{14}$ to $A_{16}$ may each independently be selected from a $C_5$-$C_{20}$ carbocyclic group and a $C_1$-$C_{20}$ heterocyclic group, $R_{31}$ to $R_{38}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{10}$ arylthio group, a $C_1$-$C_{60}$ heteroaryl group, a monovalent non-aromatic condensed polycyclic group, and a monovalent non-aromatic condensed heteropolycyclic group.

For example, $A_{14}$ to $A_{16}$ in Formulae 1-11 to 1-19 may each independently be selected from a $C_5$-$C_{20}$ cycloalkane, a $C_5$-$C_{20}$ cycloalkene, a $C_5$-$C_{20}$ arene, a $C_1$-$C_{20}$ heterocycloalkane, a $C_1$-$C_{20}$ heterocycloalkene, and a $C_1$-$C_{20}$ heteroarene, but are not limited thereto.

In various embodiments, $A_{14}$ to $A_{16}$ in Formulae 1-11 to 1-19 may each independently be selected from a benzene, a naphthalene, a fluorene, an indene, a furan, a thiophene, a carbazole, a benzofuran, a benzothiophene, a dibenzofuran, and a dibenzothiophene, but are not limited thereto.

In various embodiments, $A_{14}$ to $A_{16}$ in Formulae 1-11 to 1-19 may each independently be selected from a benzene and a naphthalene, but are not limited thereto.

In various embodiments, $A_{11}$ to $A_{13}$ in Formulae 1-11 to 1-19 may each independently be selected from a pyrrole, an imidazole, a pyrazole, a triazole, a pyridine, a pyrimidine, a pyrazine, a pyridazine, a triazine, a quinoline, an isoquinoline, an indole, an isoindole, a benzimidazole, and an indazole, and $A_{14}$ to $A_{18}$ may each independently be selected from a benzene, a naphthalene, a fluorene, an indene, a furan, a thiophene, a carbazole, a benzofuran, a benzothiophene, a dibenzofuran, and a dibenzothiophene, but are not limited thereto.

For example, $R_{31}$ to $R_{38}$ in Formulae 1-11 to 1-19 may each independently be selected from hydrogen, —F, a cyano group, a methyl group, an ethyl group, an iso-propyl group, a tert-butyl group, and —CF$_3$, but are not limited thereto.

In various embodiments, $R_{31}$ to $R_{38}$ in Formulae 1-11 to 1-19 may be all hydrogen, but are not limited thereto.
In various embodiments, the organometallic compound represented by Formula 1 may be selected from Compounds 1 to 50, but is not limited thereto:
1
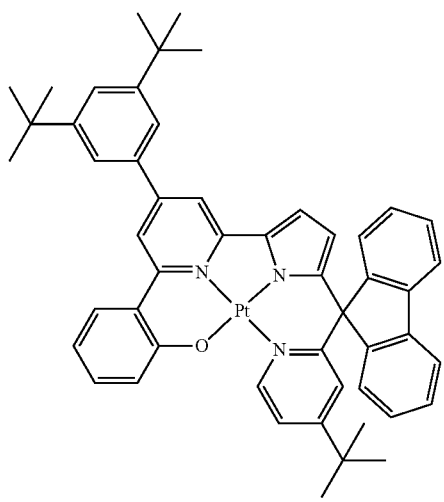
2
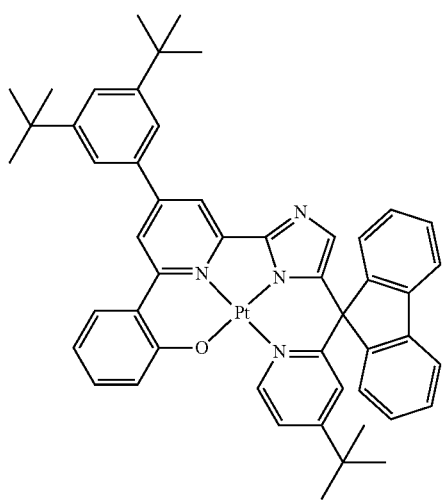
3
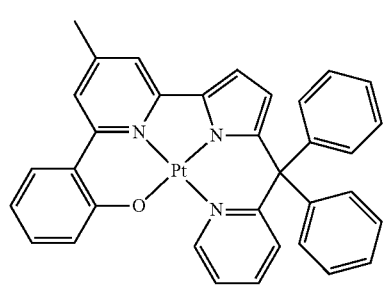
-continued
4
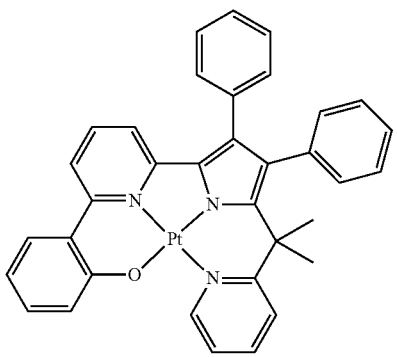
5
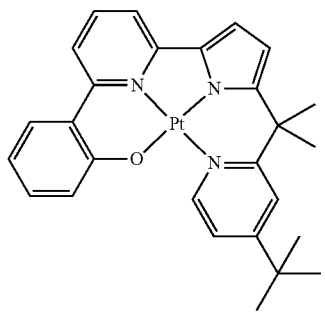
6
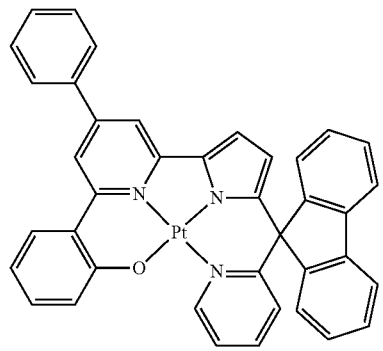
7
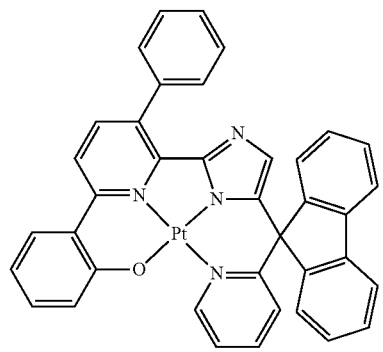

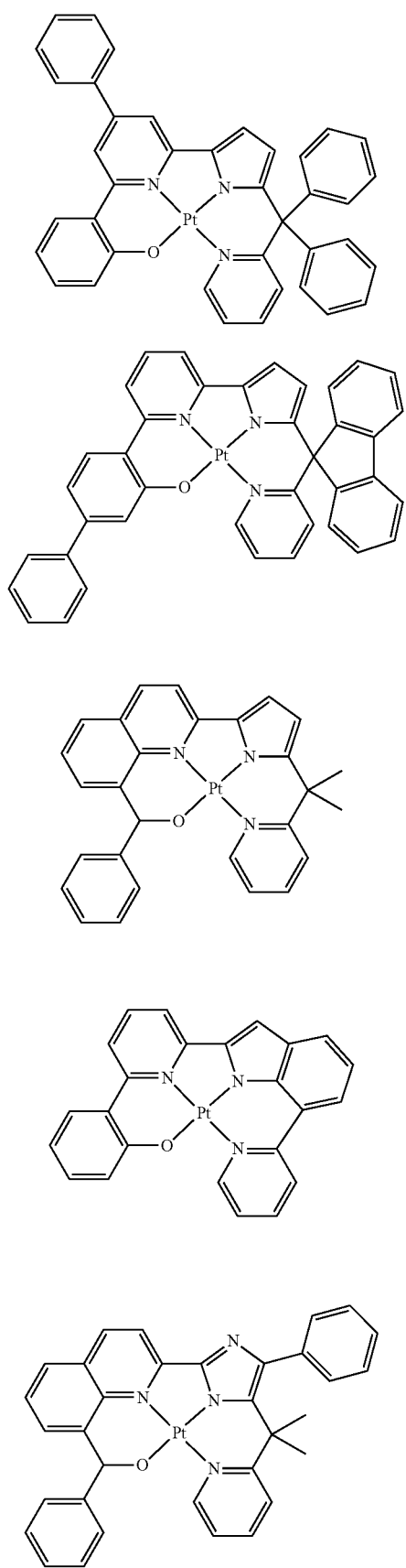
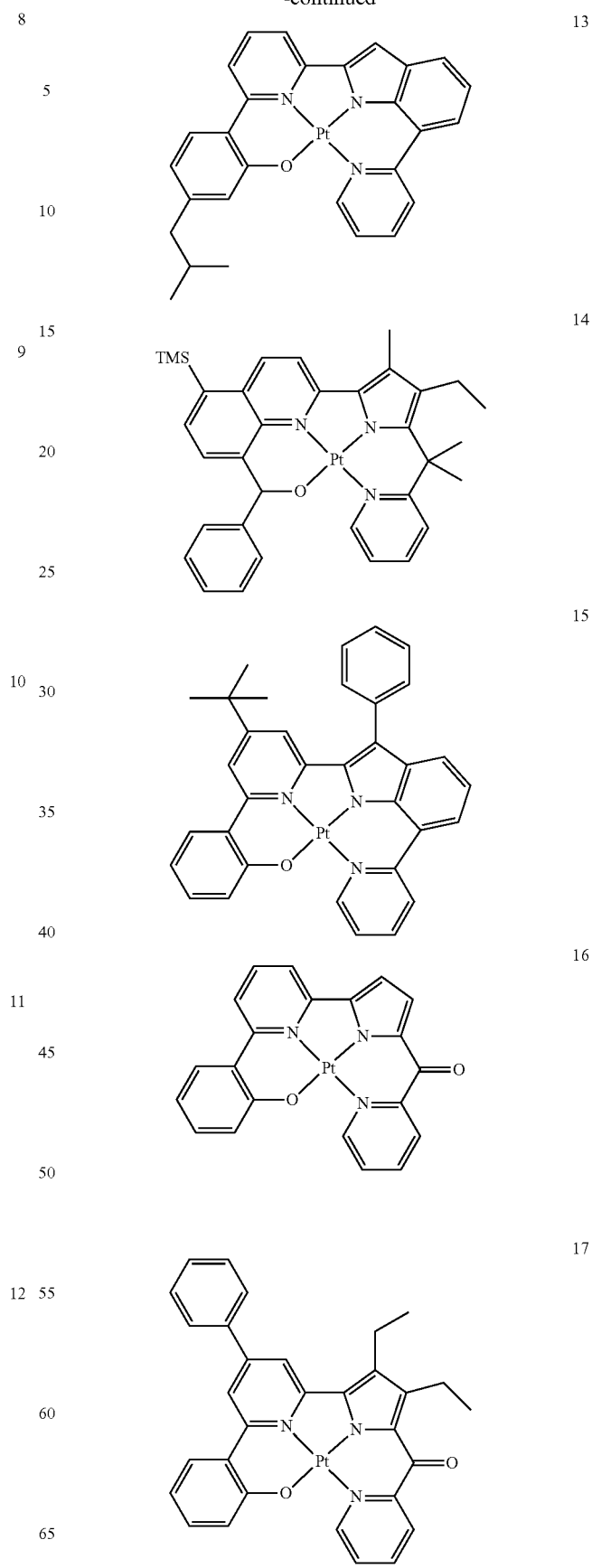

18
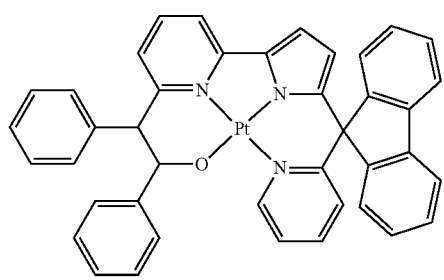
19
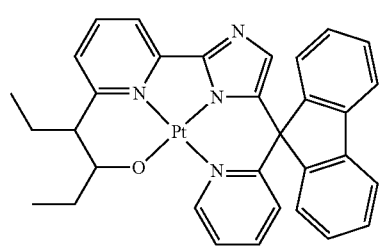
20
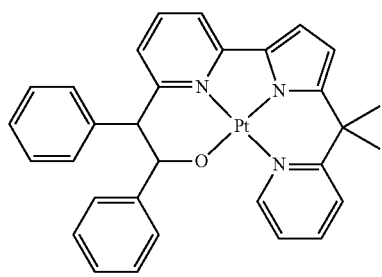
21
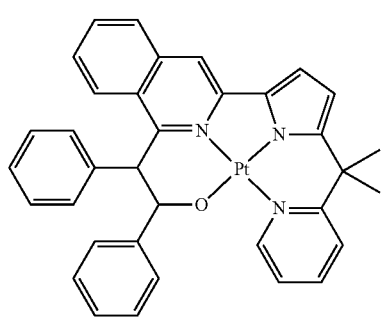
22
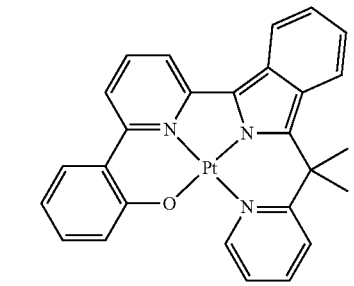
23
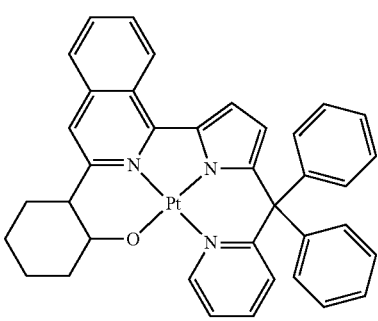
24
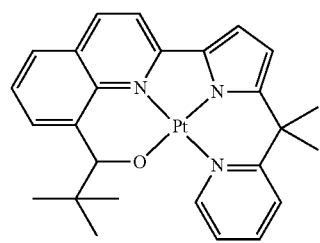
25
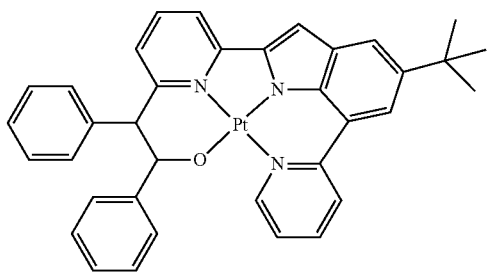
26
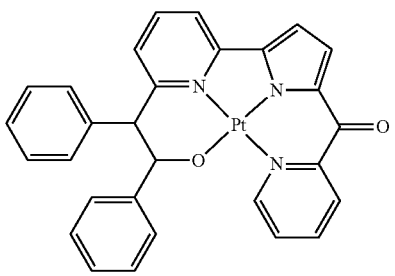
27
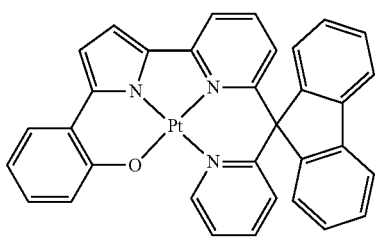
28
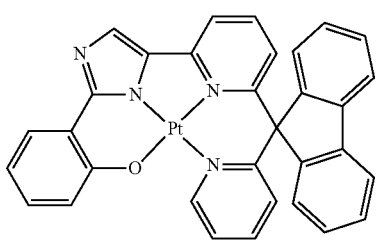

29
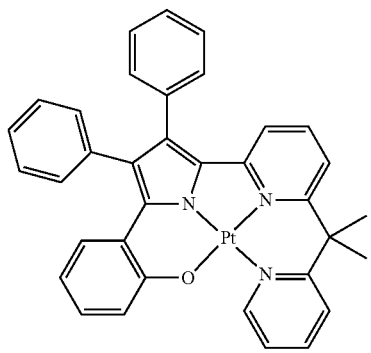
30
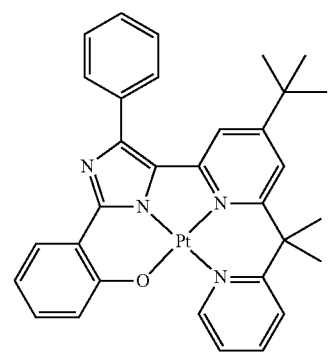
31
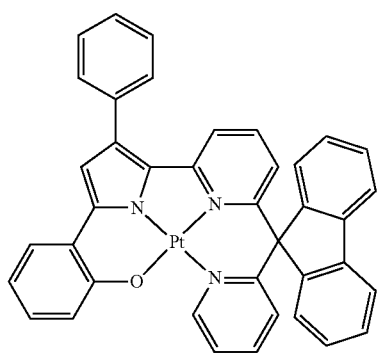
32
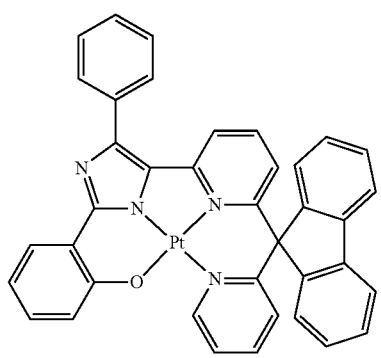
33
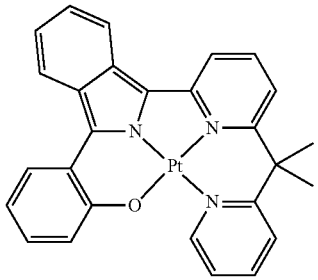
34
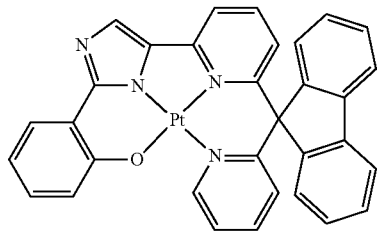
35
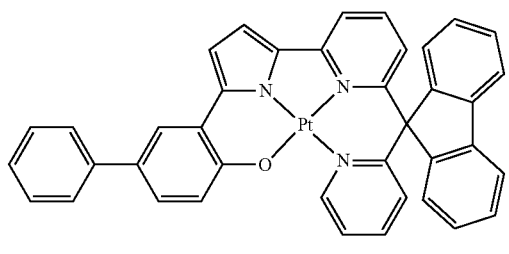
36
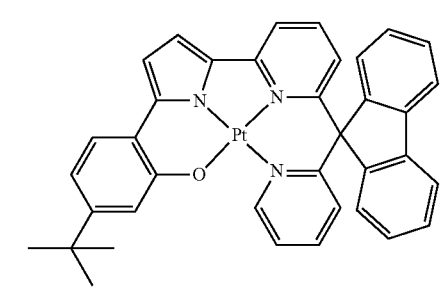
37
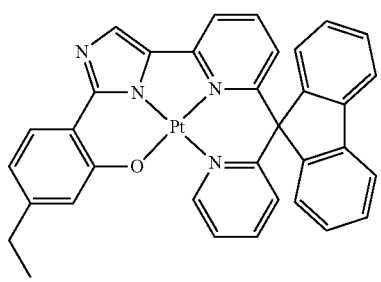

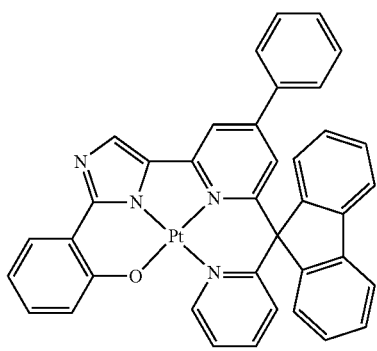
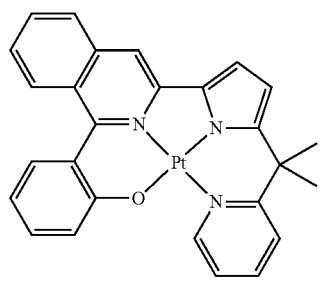
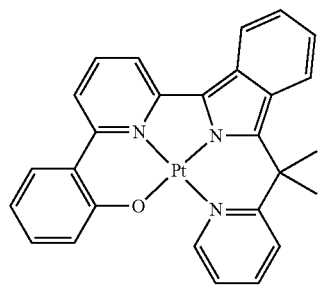
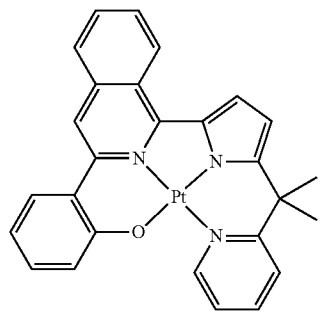
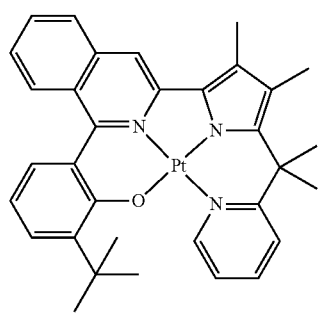
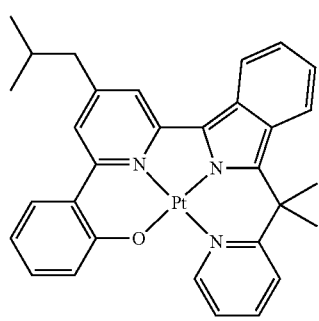
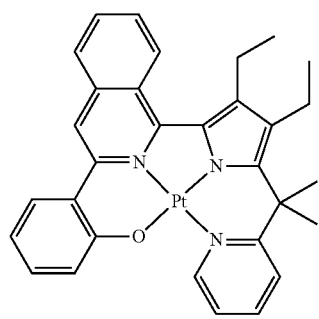
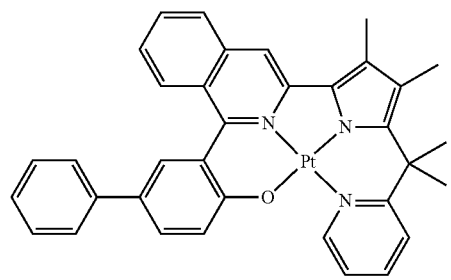
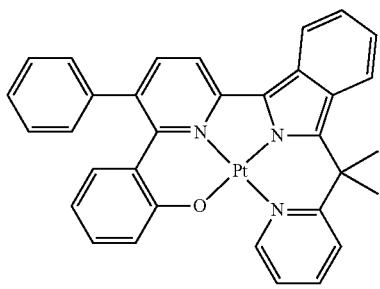
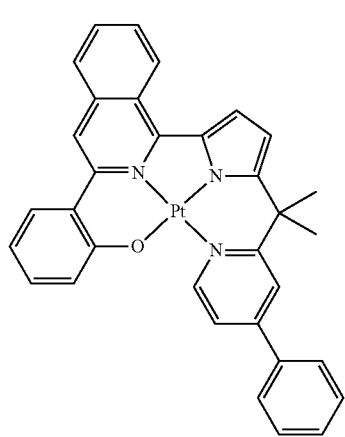

48

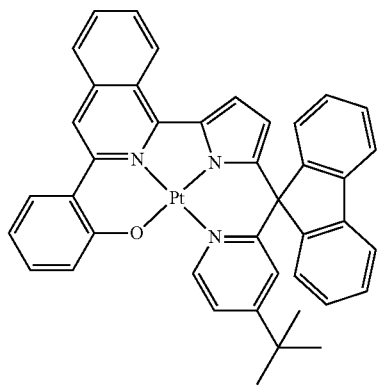

49

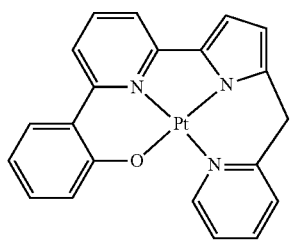

50

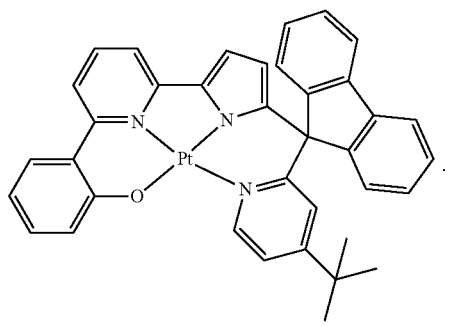

In Compounds 1 to 50, TMS may be a trimethylsilyl group represented by —Si(CH$_3$)$_3$.

The organometallic compound represented by Formula 1 may emit green light or red light. In particular, the organometallic compound represented by Formula 1 may emit green phosphorescence or red phosphorescence. A maximum emission wavelength of the organometallic compound represented by Formula 1 may be in a range of about 500 nanometers (nm) to about 640 nm.

The organometallic compound represented by Formula 1 may include a substituent (for example, a substituent including a spiro-structure) at a location marked in Formula 1', thereby providing an organic light-emitting device having a reduced roll-off phenomenon:

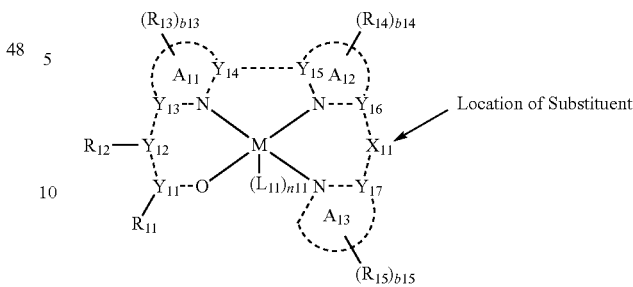

Formula 1'

Due to the substituent at the marked location, the compound may not have a planar structure. Accordingly, since the compound does not have the planar structure, an interaction between the compounds (for example, n-T stacking) may be reduced, and the roll-off phenomenon may be reduced in the organic light-emitting device including the compound.

In the organometallic compound represented by Formula 1, a metal (M) may be bonded to one oxygen atom and three nitrogen atoms. Accordingly, the organic light-emitting device including the organometallic compound represented by Formula 1 may have a low driving voltage, high efficiency, high luminance, and a long lifespan.

For example, the HOMO energy level, LUMO energy level, band gap, S$_1$ (singlet) energy level, T$_1$ (triplet) energy level, and maximum emission wavelength of some of the organometallic compounds represented by Formula 1 and Compound A were evaluated by using a Gaussian 09 program, followed by a molecular structure optimization using a density functional theory (DFT) based on B3LYP. Results thereof are shown in Table 1.

TABLE 1

|  | HOMO (eV) | LUMO (eV) | Band gap (eV) | S$_1$ (eV) | T$_1$ (eV) |
|---|---|---|---|---|---|
| Compound 2 | −4.916 | −1.599 | 3.317 | 2.749 | 2.500 |
| Compound 1 | −4.714 | −1.484 | 3.230 | 2.665 | 2.387 |
| Compound 48 | −4.697 | −1.673 | 3.024 | 2.475 | 1.933 |
| Compound A | −4.727 | −1.598 | 3.129 | 2.566 | 2.318 |

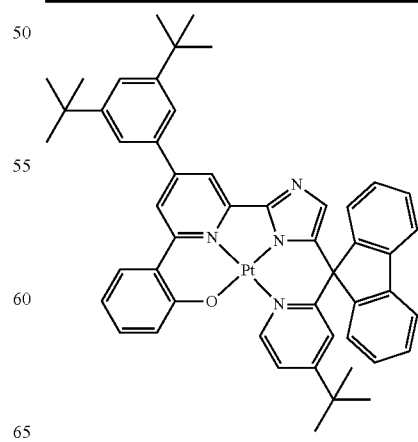

2

TABLE 1-continued

| HOMO (eV) | LUMO (eV) | Band gap (eV) | S₁ (eV) | T₁ (eV) |
|---|---|---|---|---|

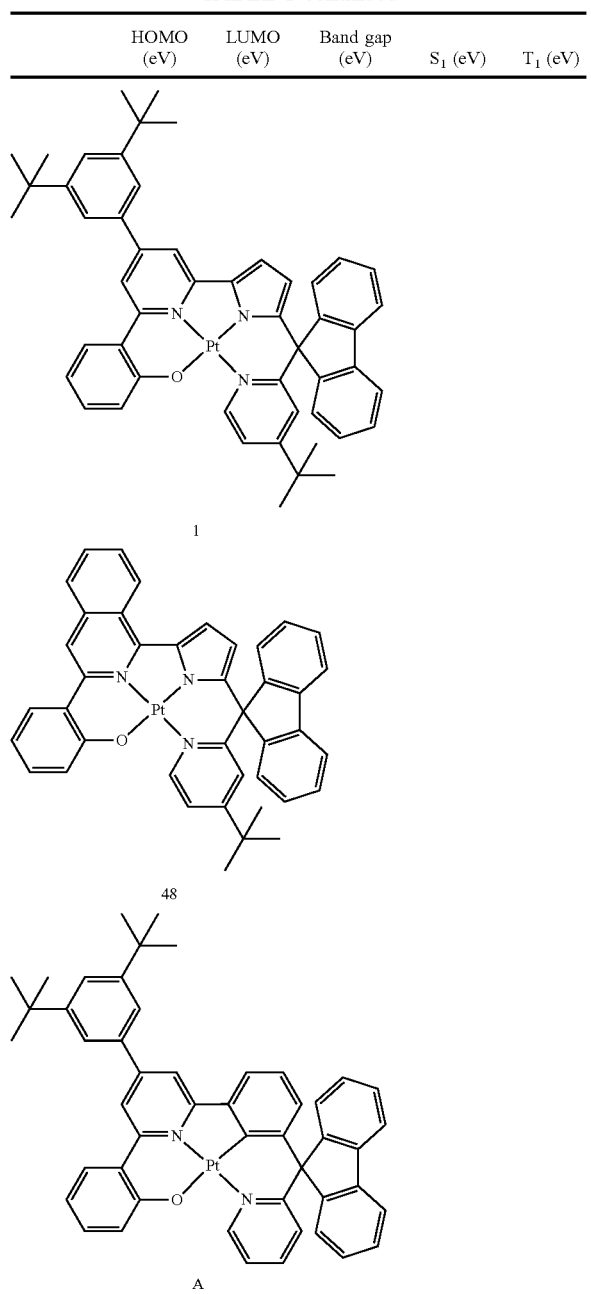

Synthesis methods of the organometallic compound represented by Formula 1 may be easily recognized by one of ordinary skill in the art by referring to Synthesis Examples provided below.

The organometallic compound represented by Formula 1 is suitable for use in an organic layer of an organic light-emitting device, for example, for use as a dopant in an emission layer of the organic layer. Thus, another aspect provides an organic light-emitting device that includes:

a first electrode;
a second electrode; and
an organic layer disposed between the first electrode and the second electrode, wherein the organic layer includes an emission layer and the organometallic compound represented by Formula 1.

The organic light-emitting device may have, due to the inclusion of an organic layer including the organometallic compound represented by Formula 1, high efficiency, a long lifespan, and high color purity.

The organometallic compound of Formula 1 may be disposed between a pair of electrodes of an organic light-emitting device. For example, the organometallic compound represented by Formula 1 may be included in the emission layer. The organometallic compound may act as a dopant and in this case, the emission layer may further include a host. The emission layer may emit red light or green light.

The expression that "(an organic layer) includes an organometallic compound" as used herein may include a case in which "(an organic layer) includes identical organometallic compounds represented by Formula 1 and a case in which (an organic layer) includes two or more different organometallic compounds represented by Formula 1.

For example, the organic layer may include, as the organometallic compound, only Compound 1. In this regard, Compound 1 may be included in an emission layer of the organic light-emitting device. In some embodiments, the organic layer may include, as the organometallic compound, Compound 1 and Compound 2. In this regard, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" as used herein refers to a single layer and/or a plurality of layers disposed between the first electrode and the second electrode of the organic light-emitting device. The "organic layer" may include, in addition to an organic compound, an organometallic complex including metal.

FIG. 1 is a schematic view of an organic light-emitting according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

In various embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). In some embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, 1-NPB, TPD, Spiro-TPD, Spiro-NPB, methylated NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

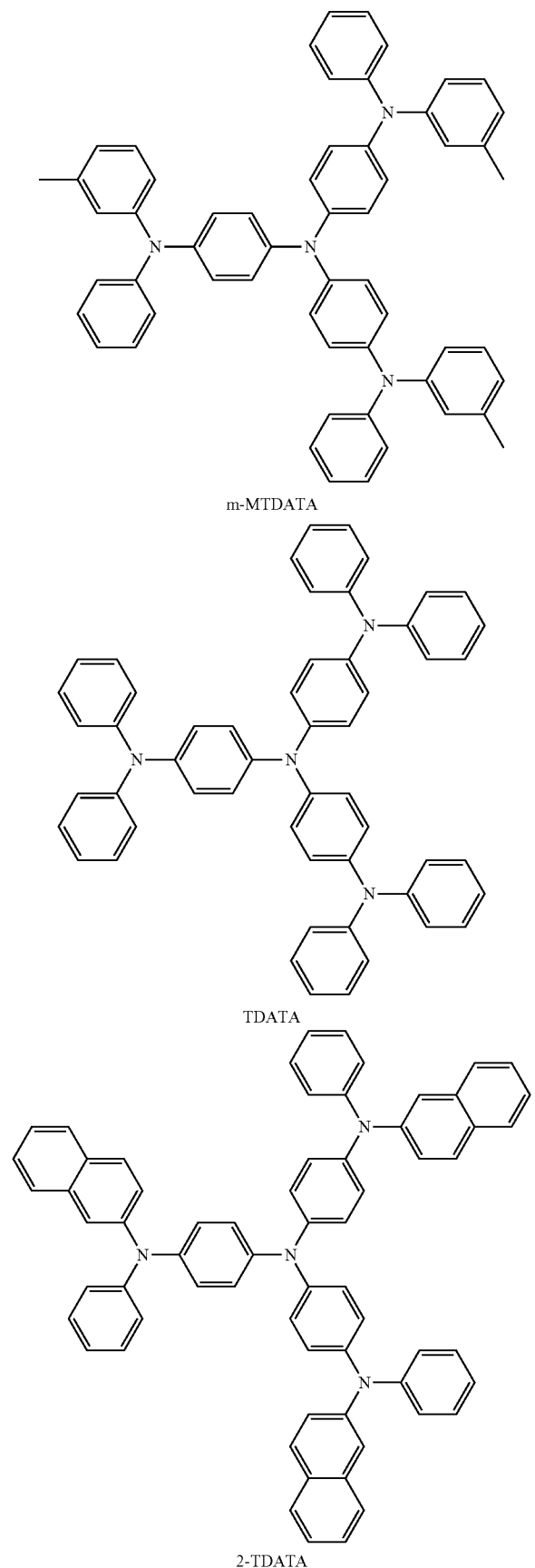

m-MTDATA

TDATA

2-TDATA

-continued
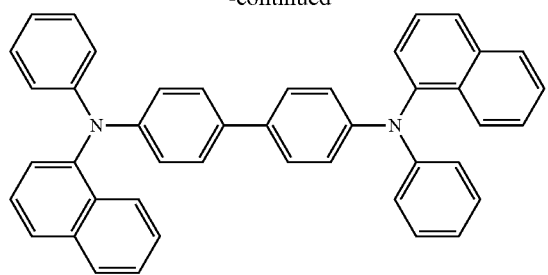
NPB
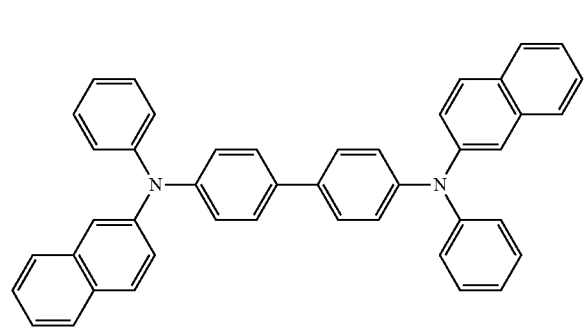
β-NPB
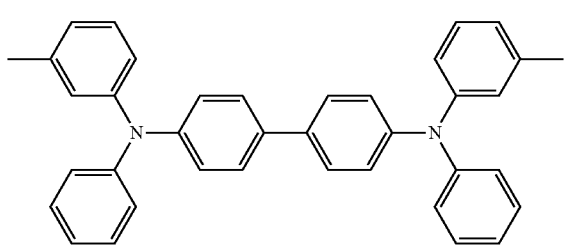
TPD
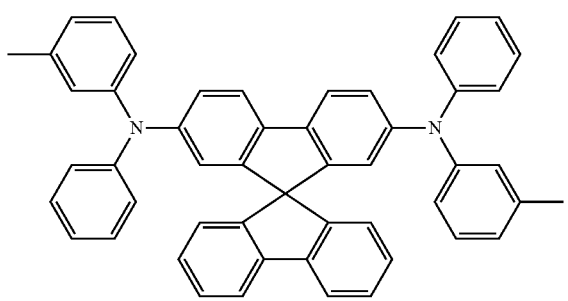
Spiro-TPD
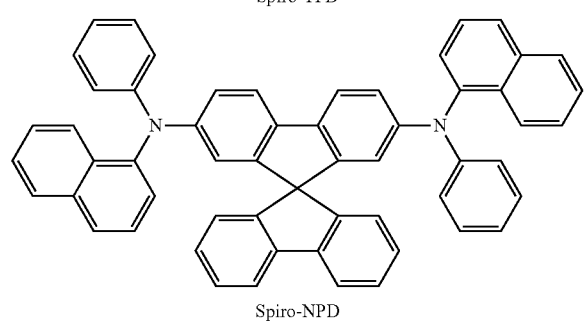
Spiro-NPD
-continued
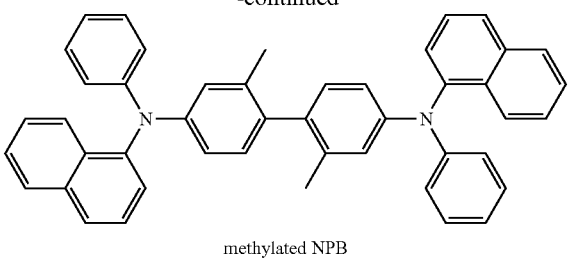
methylated NPB
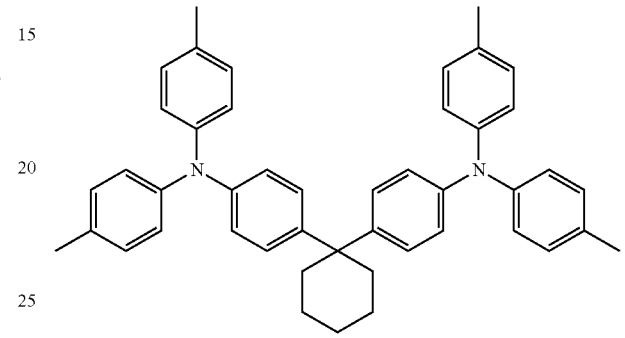
TAPC
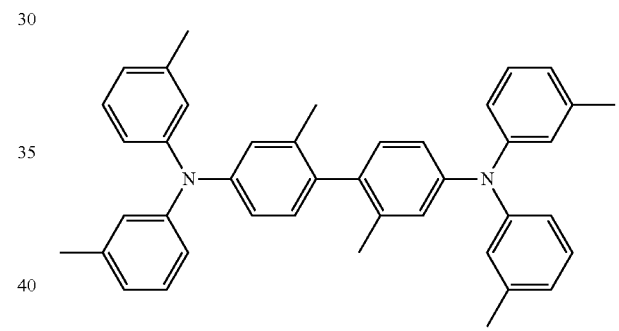
HMTPD
Formula 201
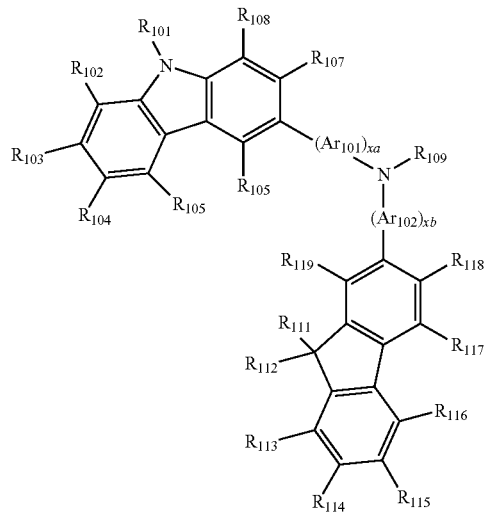

-continued

Formula 202

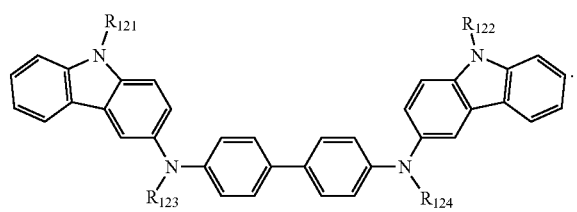

$Ar_{101}$ and $Ar_{102}$ in Formula 201 may each independently be selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{10}$ arylthio group, a $C_2$-$C_{60}$ heteroaryl group, a monovalent non-aromatic condensed polycyclic group, and a monovalent non-aromatic condensed heteropolycyclic group.

xa and xb in Formula 201 may each independently be an integer selected from 0 to 5, or 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A below, but is not limited thereto:

Formula 201A

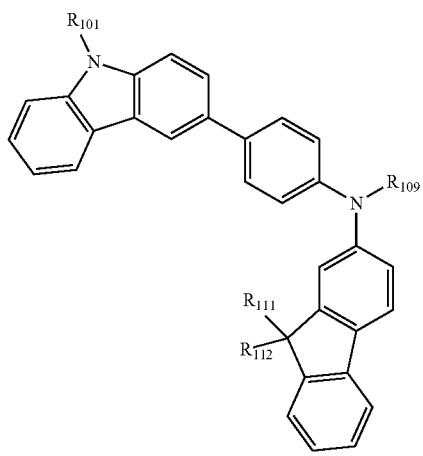

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

HT1
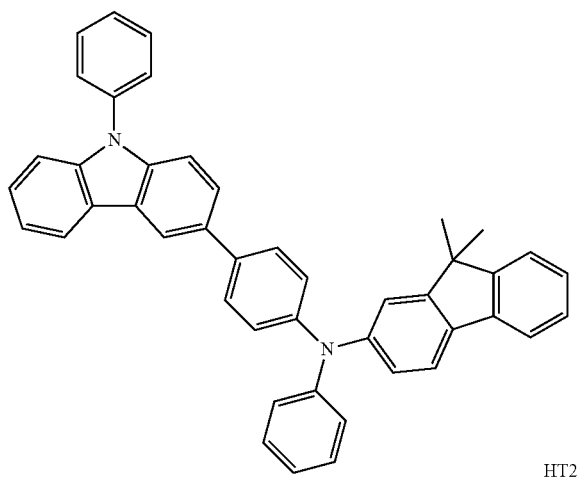
HT2
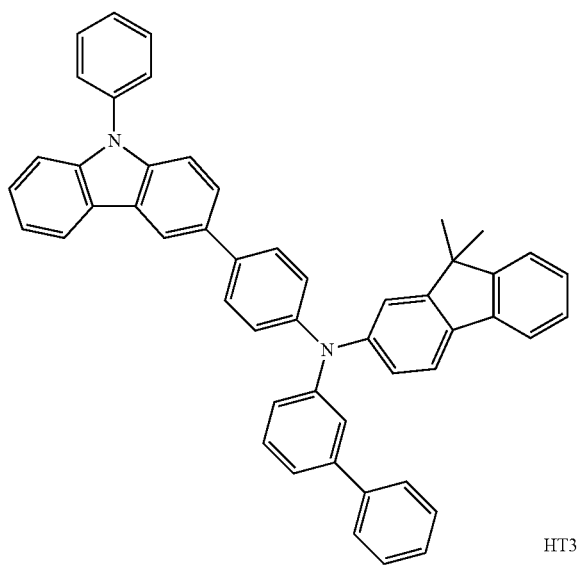
HT3
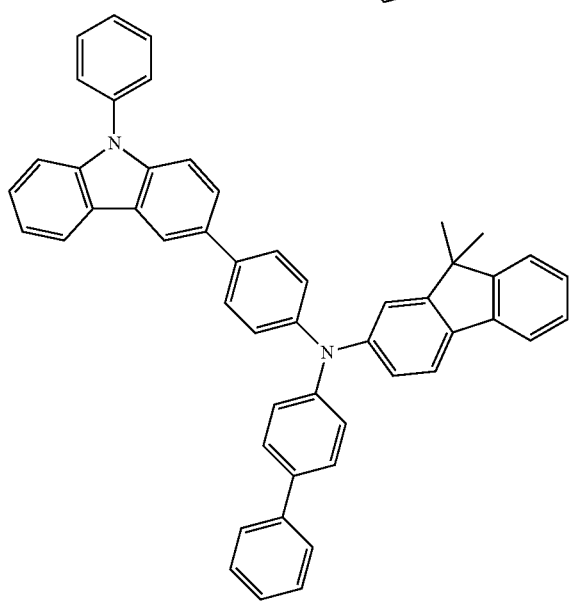
HT4
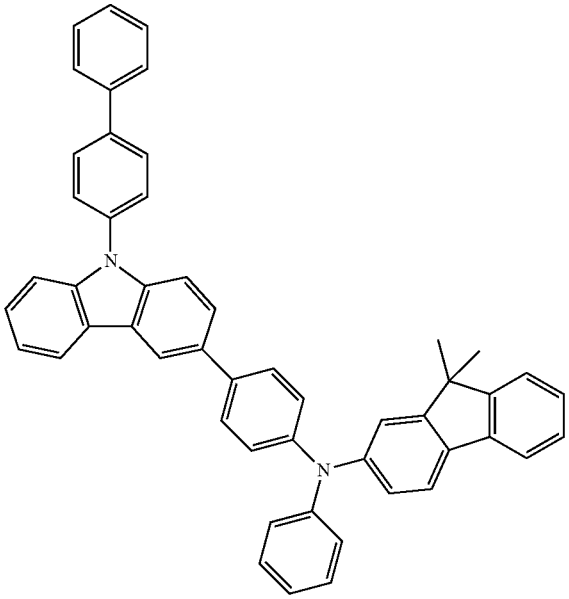
HT5

HT6
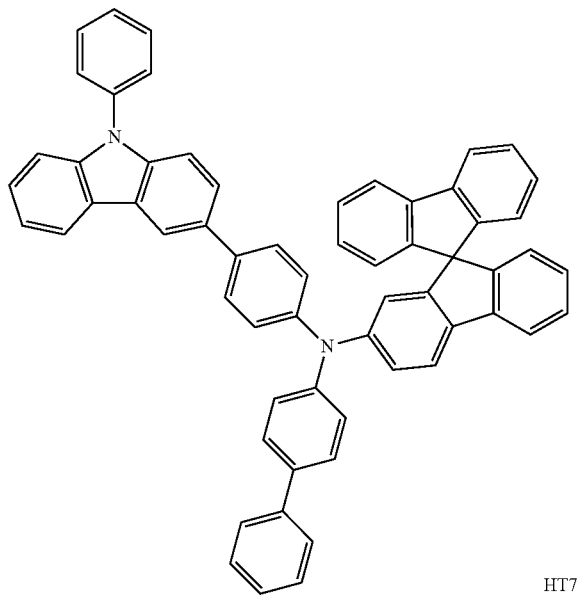
HT7
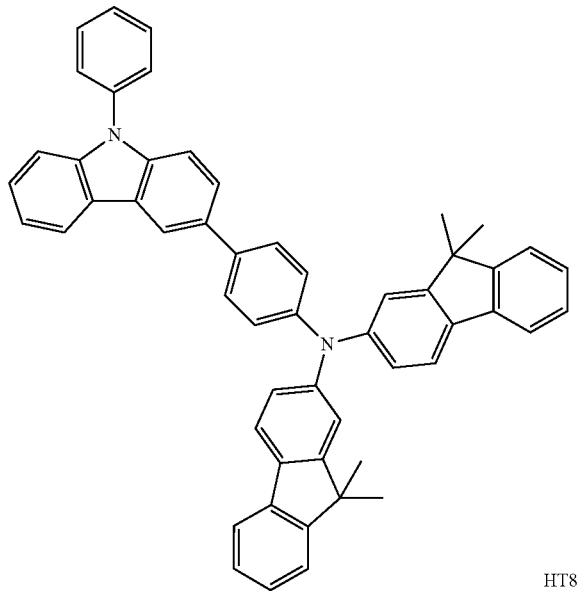
HT8
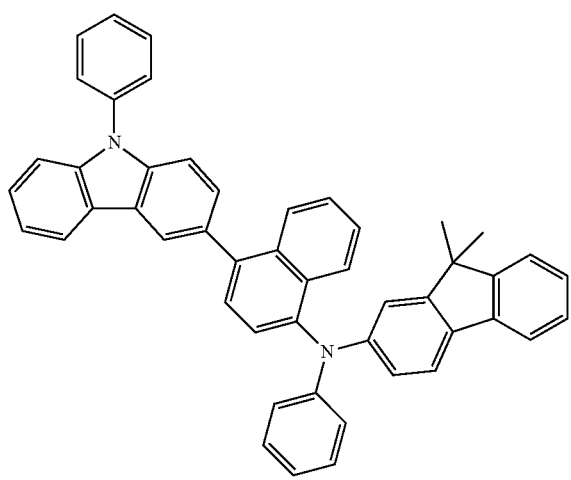
HT9
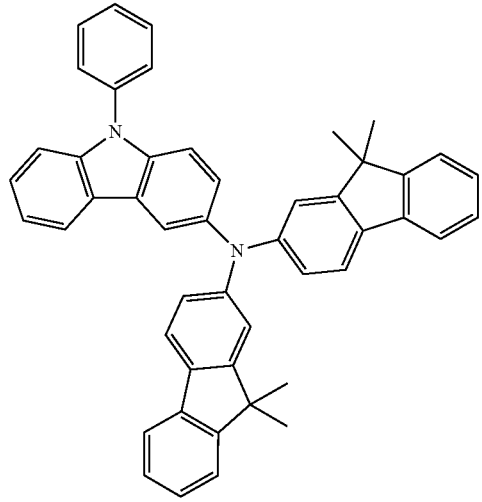
HT10
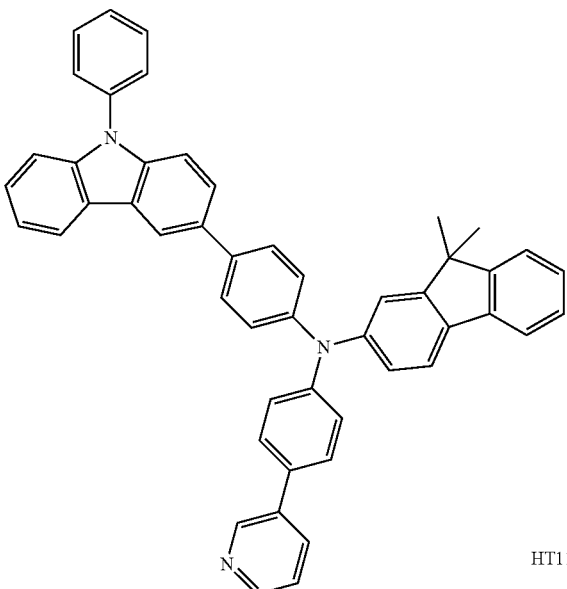
HT11
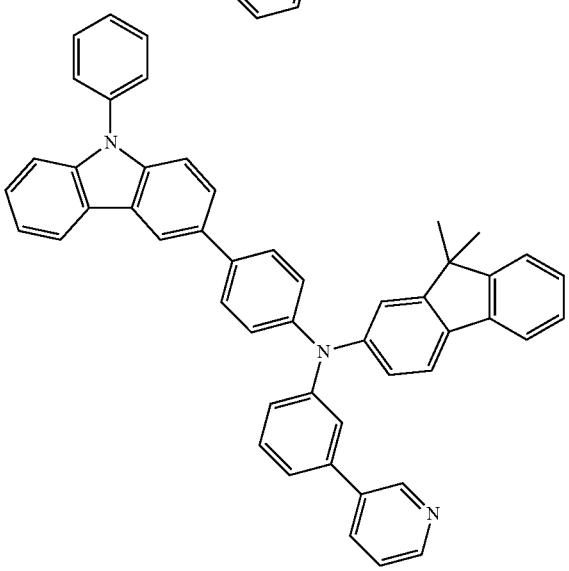

HT12
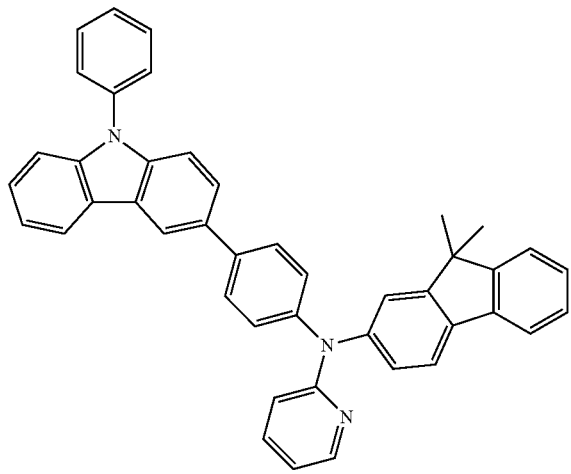
HT16
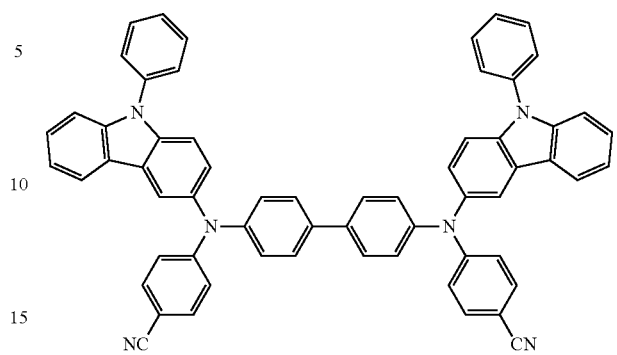
HT13
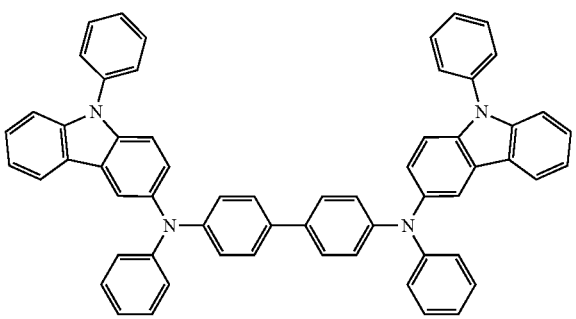
HT17
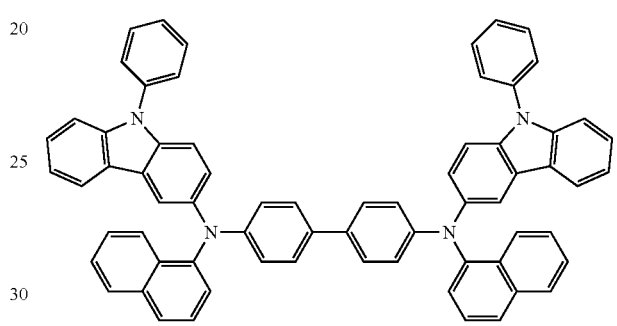
HT14
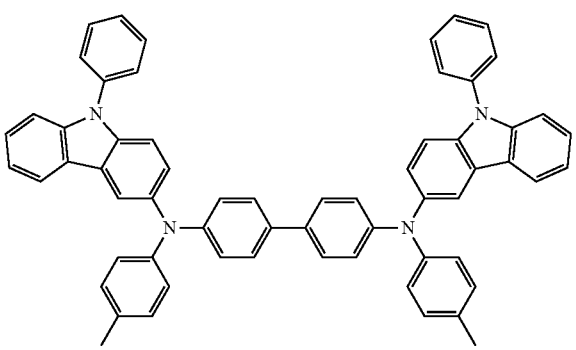
HT18
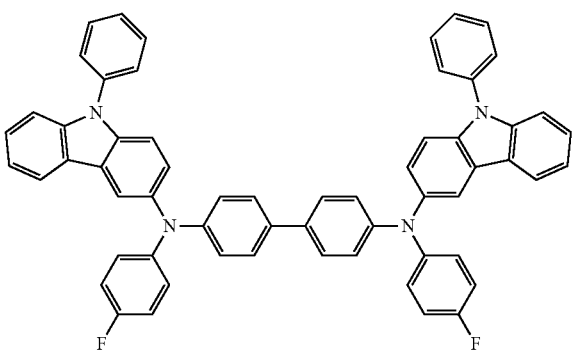
HT15
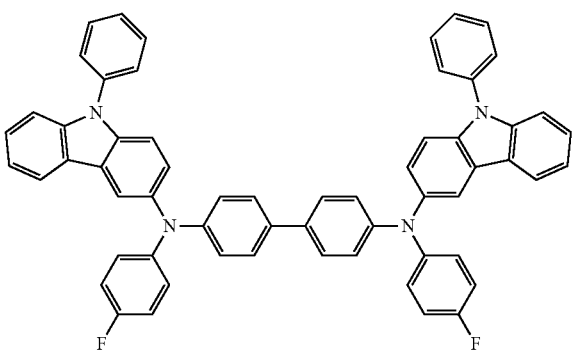
HT19
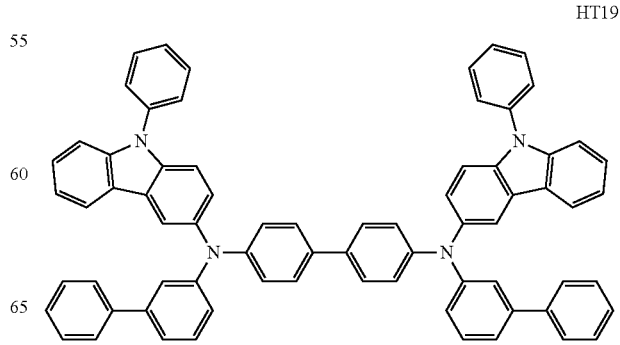

HT20

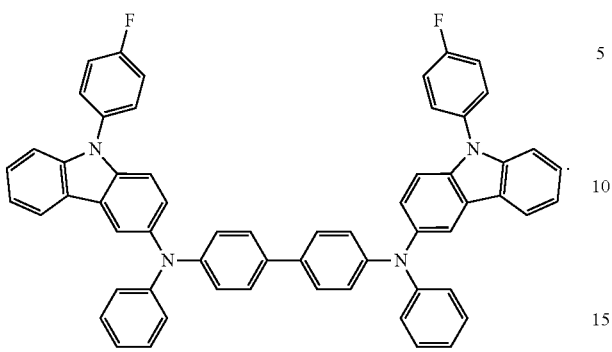

A thickness of the hole transport region may be in a range of about 100 Å to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is believed that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

Compound HT-D1

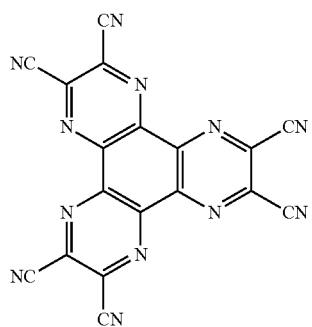

F4-TCNQ

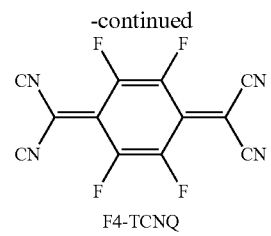

Compound HT-D2

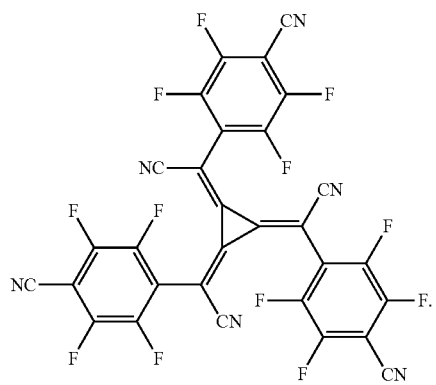

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant.

The host may include at least one selected from CBP, CDBP, TCP, and mCP:

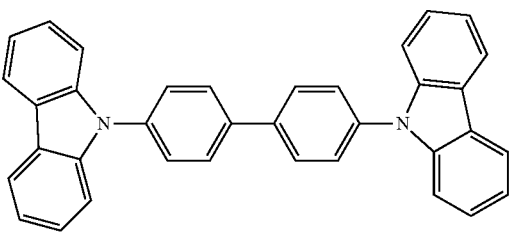

CPB

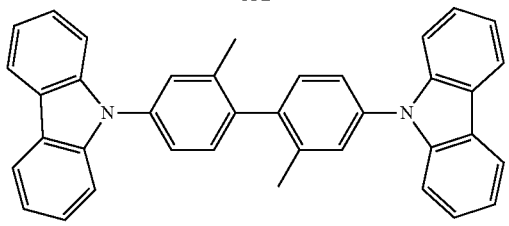

CDPB

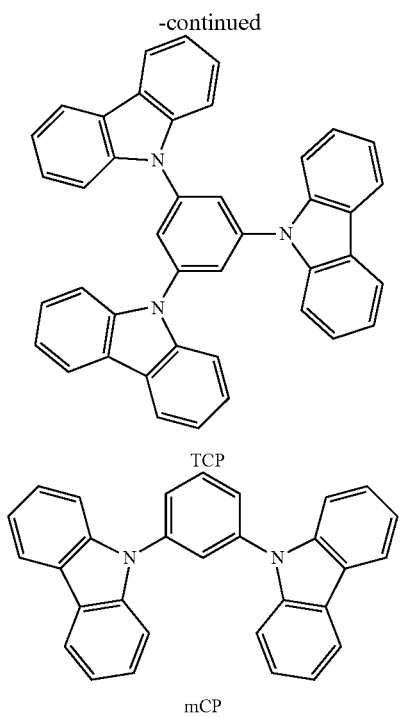

TCP mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include, as a dopant, the organometallic compound represented by Formula 1.

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is believed that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

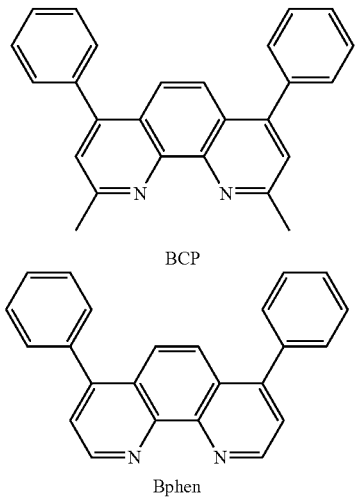

BCP

Bphen

A thickness of the hole blocking layer may be in a range of about 20 Å to about 1,000 Å, for example, about 30 Å to about 300 Å. While not wishing to be bound by theory, it is believed that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, Balq, TAZ, and NTAZ.

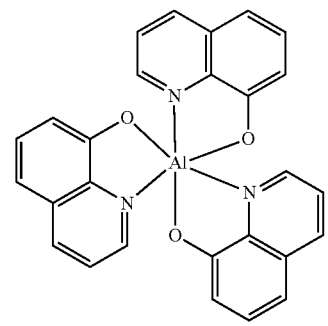

Alq$_3$

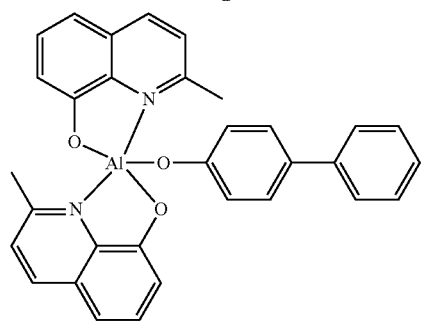

BAlq

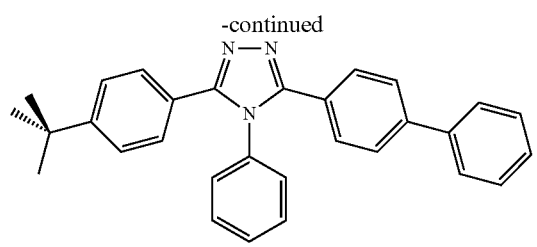
TAZ
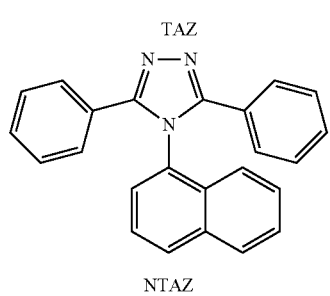
NTAZ
In various embodiments, the electron transport layer may include at least one of ET1 and ET19, but are not limited thereto:
ET1
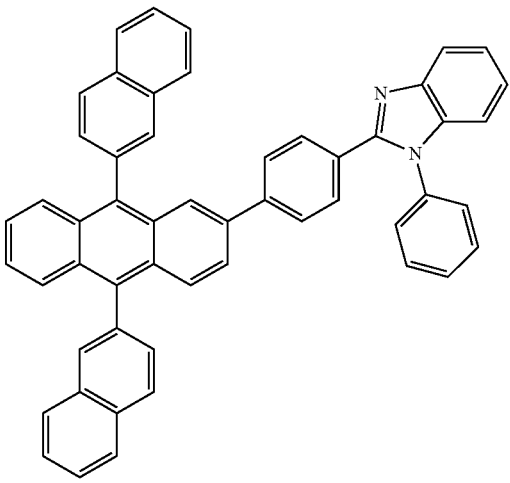
ET2
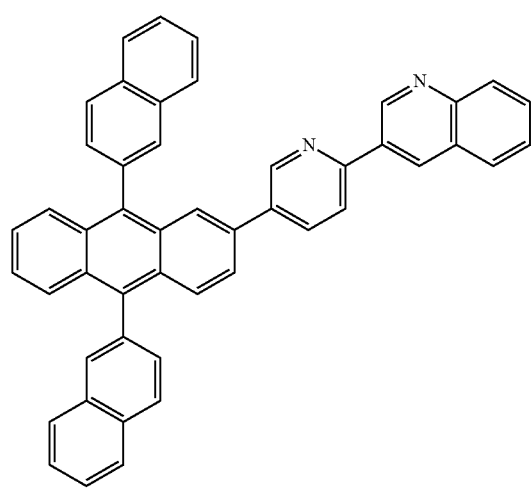
ET3
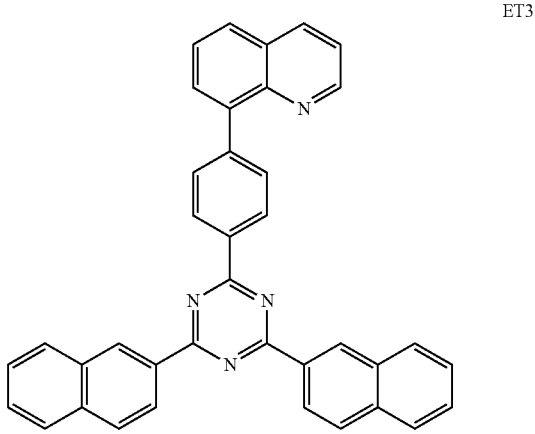
ET4
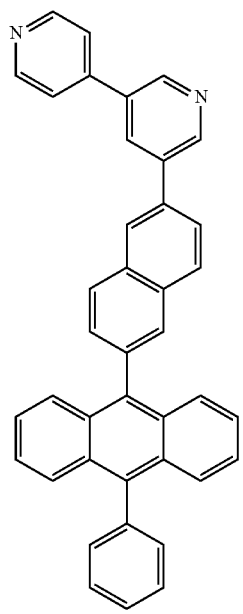
ET5
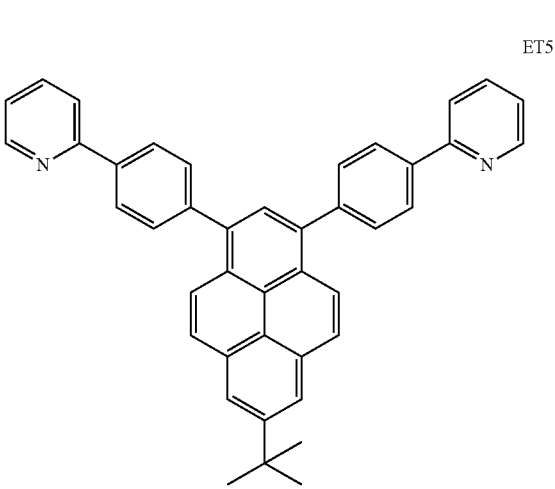

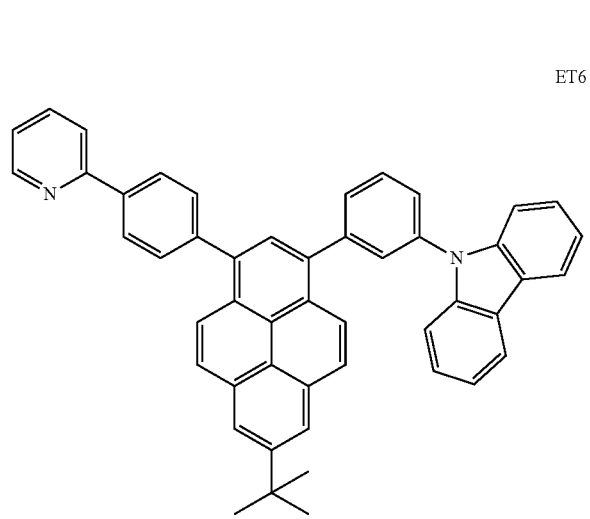
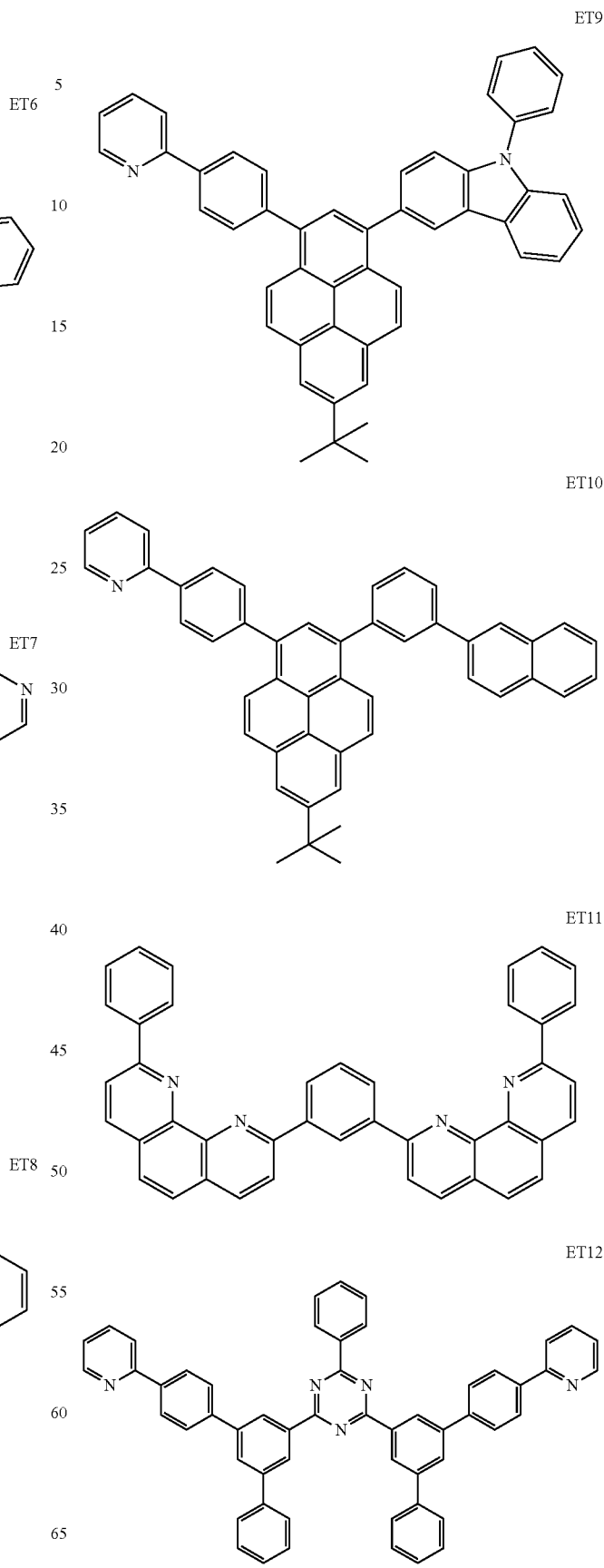

ET13
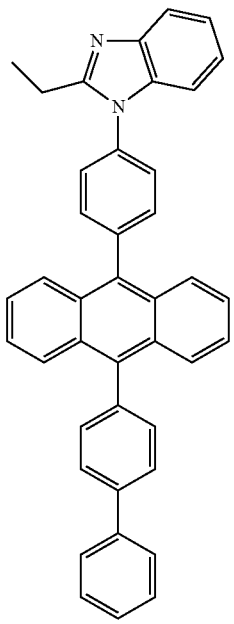
ET14
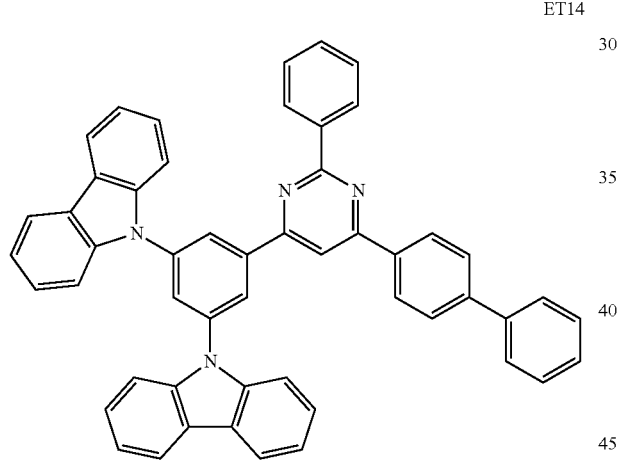
ET15
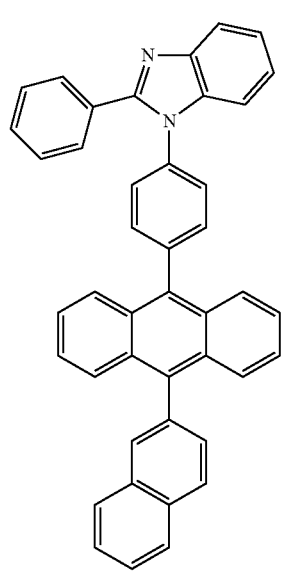
ET16
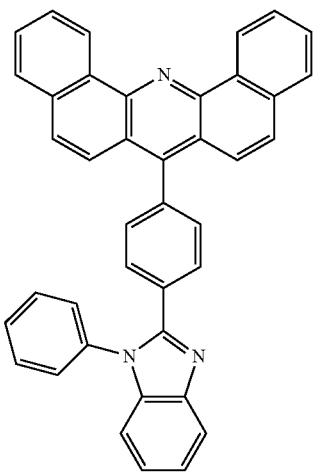
ET17
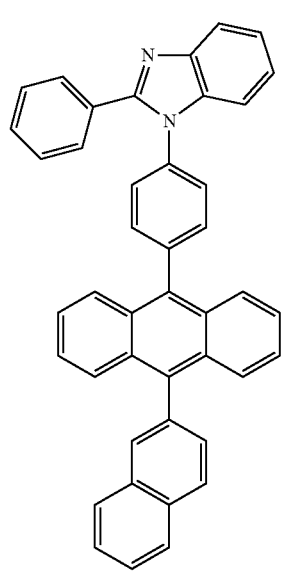
ET18
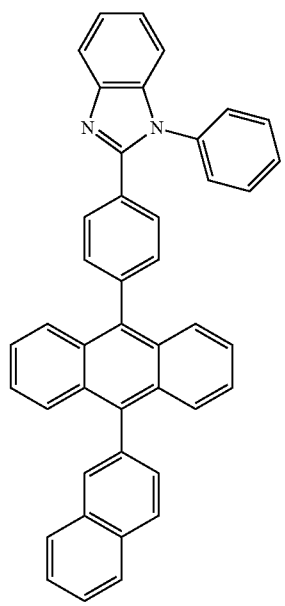

ET19

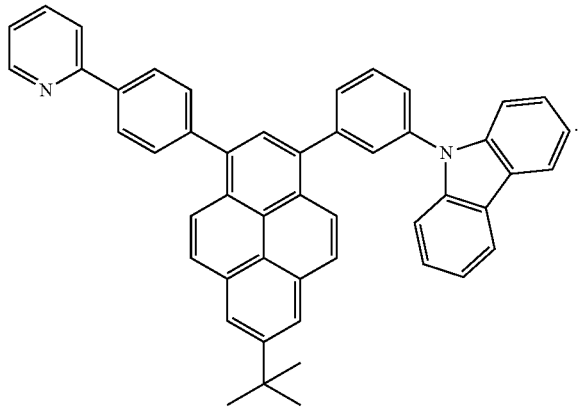

A thickness of the electron transport layer may be in a range of about 100 Å to about 1,000 Å, for example, about 150 Å to about 500 Å. While not wishing to be bound by theory, it is believed that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

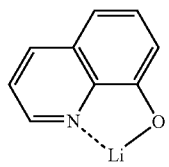

ET-D2

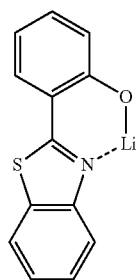

The electron transport layer may include an electron injection layer (EIL) that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. While not wishing to be bound by theory, it is believed that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{30}$ alkyl group," as used herein, refers to a linear or branched aliphatic hydrocarbon monovalent group having 1 to 60 carbon atoms. Examples thereof include a methyl group, an ethyl group, a propyl group, an isobutyl group, a sec-butyl group, a tert-butyl group, a pentyl group, an iso-amyl group, and a hexyl group.

The term "$C_3$-$C_{30}$ branched alkyl group," as used herein refers to a monovalent branched aliphatic hydrocarbon group having 3 to 30 carbon atoms, and may be, for example, selected from $C_3$-$C_{30}$ alkyl groups excluding a linear alkyl group, such as an n-propyl group. Examples of the $C_3$-$C_{30}$ branched alkyl group include an iso-propyl group and a tert-butyl group.

The term "$C_1$-$C_{30}$ alkoxy group," as used herein, refers to a monovalent group represented by —$OA_{101}$ (wherein $A_{101}$ is the $C_1$-$C_{30}$ alkyl group). Examples thereof include a methoxy group, an ethoxy group, and an isopropyloxy group.

The term "$C_2$-$C_{30}$ alkenyl group," as used herein, refers to a hydrocarbon group having at least one carbon double bond in the middle or at the terminal of the $C_2$-$C_{30}$ alkyl group. Examples thereof include an ethenyl group, a propenyl group, and a butenyl group.

The term "$C_2$-$C_{30}$ alkynyl group," as used herein, refers to a hydrocarbon group having at least one carbon triple bond in the middle or at the terminal of the $C_2$-$C_{30}$ alkyl group. Examples thereof include an ethynyl group and a propynyl group.

The term "$C_3$-$C_{10}$ cycloalkyl group," as used herein, refers to a monovalent hydrocarbon monocyclic group having 3 to 10 carbon atoms. Examples thereof include a cyclopropyl group, a cyclobutyl group, a cyclopentyl group, a cyclohexyl group, and a cycloheptyl group.

The term "$C_1$-$C_{10}$ heterocycloalkyl group," as used herein, refers to a monovalent monocyclic group having at least one heteroatom selected from N, O, P, and S as a ring-forming atom and 1 to 10 carbon atoms. Examples thereof are a tetrahydrofuranyl group, and a tetrahydrothiophenyl group.

The term "$C_3$-$C_{10}$ cycloalkenyl group," as used herein, refers to a monovalent monocyclic group that has 3 to 10 carbon atoms and at least one double bond in the ring thereof, and which is not aromatic. Examples thereof are a cyclopentenyl group, a cyclohexenyl group, and a cycloheptenyl group.

The term "$C_1$-$C_{10}$ heterocycloalkenyl group," as used herein, refers to a monovalent monocyclic group that has at least one heteroatom selected from N, O, P, and S as a ring-forming atom, 1 to 10 carbon atoms, and at least one double bond in its ring. Examples of the $C_1$-$C_{10}$ heterocycloalkenyl group are a 2,3-dihydrofuranyl group and a 2,3-dihydrothiophenyl group.

The term "$C_6$-$C_{60}$ aryl group," as used herein refers to a monovalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group includes two or more rings, the rings may be fused to each other.

The term "$C_1$-$C_{60}$ heteroaryl group," as used herein, refers to a monovalent carbocyclic aromatic system having at least one heteroatom selected from N, O, P, and S as a ring-forming atom and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group includes two or more rings, the rings may be fused to each other.

A monovalent non-aromatic condensed polycyclic group as used herein refers to a monovalent group that has two or more rings condensed to each other, only carbon atoms as a ring forming atom, and which is non-aromatic in the entire molecular structure. Examples of the monovalent non-aromatic condensed polycyclic group are a fluorenyl group.

A monovalent non-aromatic condensed heteropolycyclic group as used herein refers to a monovalent group that has two or more rings condensed to each other, has a heteroatom selected from N, O, P, and S, other than carbon atoms, as a ring forming atom, and which is non-aromatic in the entire molecular structure. Examples of the monovalent non-aromatic condensed heteropolycyclic group are a carbazolyl group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring group, such as a benzene, a monovalent group, such as a phenyl group, or a divalent group, such as a phenylene group. In some embodiments, depending on the number of substituents connected to the $C_5$-$C_{60}$ carbocyclic group, the $C_5$-$C_{60}$ carbocyclic group may be a trivalent group or a tetravalent group.

A $C_1$-$C_{60}$ heterocyclic group as used herein refers to a group having the same structure as the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

The term "Ph" refers to a phenyl group, the term "t-Bu" refers to a tert-butyl group, and the term "Me" refers to a methyl group.

At least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group and a quinazolinyl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis Example 1: Synthesis of Compound 50

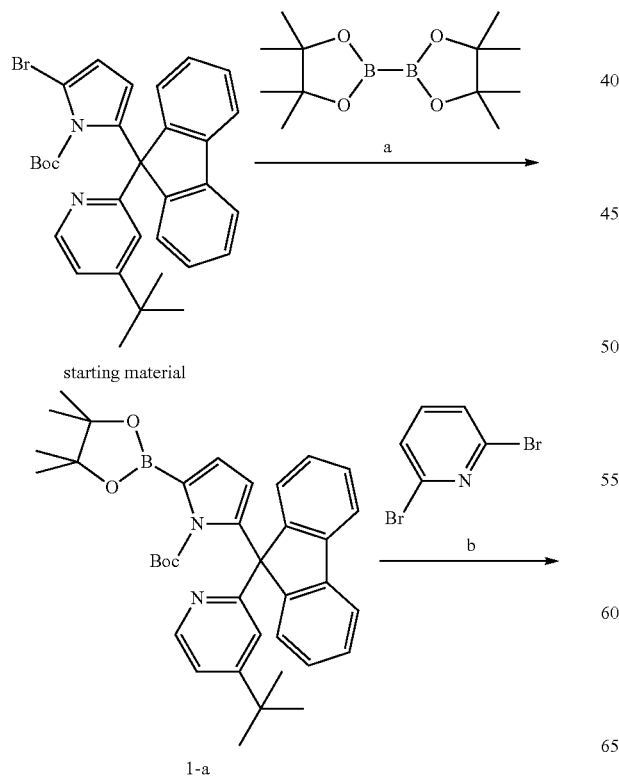

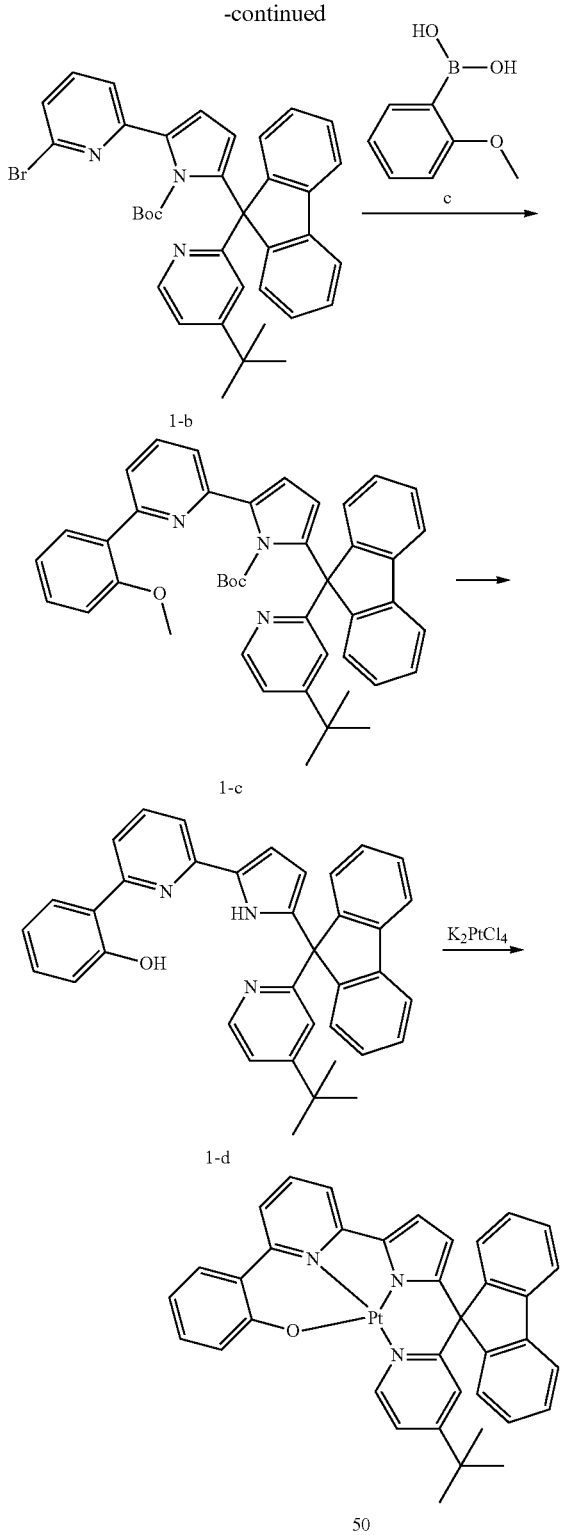

1) Synthesis of Intermediate 1-a 10 grams (g) of a starting material, 5.61 g (1.2 equivalent (eq.)) of Compound a, 1.06 g (0.05 eq.) of Pd(dppf)Cl$_2$, and 5.42 g (3 eq.) of KOAc were dissolved in 30 milliliters (mL) of toluene. The mixed solution was stirred under reflux at a temperature of 110° C. for 24 hours. After the reaction solution was cooled to room temperature, an extraction process was performed thereon using 200 mL of water three times, each time using 200 mL of diethyl ether. An organic layer collected therefrom was dried using magnesium sulfate, and a solvent was removed therefrom by evaporation. The residue obtained therefrom was purified by silica gel column chromatography, thereby completing the preparation of 8.8 g (yield: 81%) of Intermediate 1-a. The prepared compound was identified by liquid chromatography-mass spectroscopy (LC-MS).

$C_{37}H_{43}B_1N_2O_4$: $[M+H]^+$=590.33

2) Synthesis of Intermediate 1-b 5 g of Intermediate 1-a, 3.85 g (1.2 eq.) of Compound b, 0.78 g (0.05 eq.) of Pd(PPh$_3$)$_4$, and 3.99 g (3 eq.) of K$_2$CO$_3$ were dissolved in 150 mL of a tetrahydrofuran (THF) (30 mL)/H$_2$O (15 mL) to form a mixed solution. The mixed solution was stirred under reflux at a temperature of 110° C. for 24 hours. After the reaction solution was cooled to room temperature, an extraction process was performed thereon using 200 mL of water three times, each time using 200 mL of diethyl ether. An organic layer collected therefrom was dried using magnesium sulfate, and a solvent was removed therefrom by evaporation. The residue obtained therefrom was purified by silica gel column chromatography, thereby completing the preparation of 6.1 g (yield: 73%) of Intermediate 1-b. The prepared compound was identified by LC-MS.

$C_{36}H_{34}BrN_3O_2$: $[M+H]^+$=619.18

3) Synthesis of Intermediate 1-c 6 g of Intermediate 1-b, 1.76 g (1.2 eq.) of Compound c, 0.56 g (0.05 eq.) of Pd(PPh$_3$)$_4$, and 2.85 g (3 eq.) of K$_2$CO$_3$ were dissolved in a THF (22 mL)/H$_2$O (10 mL) to form a mixed solution. The mixed solution was stirred under reflux at a temperature of 110° C. for 24 hours. After the reaction solution was cooled to room temperature, an extraction process was performed thereon using 200 mL of water three times, each time using 200 mL of diethyl ether. An organic layer collected therefrom was dried using magnesium sulfate, and a solvent was removed therefrom by evaporation. The residue obtained therefrom was purified by silica gel column chromatography, thereby completing the preparation of 5.3 g (yield: 85%) of Intermediate 1-c. The prepared compound was identified by LC-MS.

$C_{43}H_{41}N_3O_3$: $[M+H]^+$=647.31

4) Synthesis of Intermediate 1-d 5 g of Intermediate 1-c and 71.35 g (80 eq.) of pyridine hydrochloride were mixed, and stirred under reflux at a temperature of 180° C. for 24 hours. After the reaction solution was cooled to room temperature, an extraction process was performed thereon using 200 mL of water three times, each time using 200 mL of diethyl ether. An organic layer collected therefrom was dried using magnesium sulfate, and a solvent was removed therefrom by evaporation. The residue obtained therefrom was purified by silica gel column chromatography, thereby completing the preparation of 2.9 g (yield: 70%) of Intermediate 1-d. The prepared compound was identified by LC-MS.

$C_{37}H_{31}N_3O_1$: $[M+H]^+$=533.25

5) Synthesis of Compound 50

2 g of Intermediate 1-d and 1.87 g (1.2 eq.) of K$_2$PtCl$_4$ were dissolved in 12 mL of acetic acid. The mixed solution was stirred under reflux at a temperature of 180° C. for 24 hours. After the reaction solution was cooled to room temperature, an extraction process was performed thereon using 200 mL of water three times, each time using 200 mL of diethyl ether. An organic layer collected therefrom was dried using magnesium sulfate, and a solvent was removed therefrom by evaporation. The residue obtained therefrom was purified by silica gel column chromatography, thereby completing the preparation of 2.1 g (yield: 77%) of Compound 50. The prepared compound was identified by LC-MS.

$C_{37}H_{29}N_3O_1Pt_1$: $[M+H]^+$=726.20

Example 1

An indium tin oxide (ITO) glass substrate, on which an ITO electrode (i.e., a first electrode or an anode) having a thickness of 1,500 Angstroms (Å) was formed, was subjected to a ultrasonic washing process using distilled water. After the washing process using distilled water was completed, the ITO glass substrate was subjected to a ultrasonic cleaning using a solvent, such as isopropyl alcohol, acetone, or methanol, followed by drying. The resulting ITO glass substrate was transported to a plasma cleaning apparatus, cleaned using oxygen plasma for 5 minutes, and then, loaded into a vacuum deposition apparatus.

Compound HT3 was vacuum deposited on the ITO glass substrate to form a first hole injection layer having a thickness of 3,500 Å. Compound HT-D1 was vacuum deposited on the first hole injection layer to form a second hole injection layer having a thickness of 300 Å. Subsequently, TAPC was vacuum deposited on the second hole injection layer to form an electron blocking layer having a thickness of 100 Å, thereby forming a hole transport region.

mCP (as a host) and Compound 50 (as a dopant, 10 percent by weight, wt %) were co-deposited on the hole transport region to form an emission layer having a thickness of 300 Å.

Compound ET3 was vacuum deposited on the emission layer to form an electron transport layer having a thickness of 250 Å. Compound ET-D1 (i.e., LiQ) was deposited on the electron transport layer to form an electron injection layer having a thickness of 5 Å. Subsequently, an Al second electrode (i.e., a cathode) having a thickness of 250 Å was formed on the electron injection layer, thereby completing the manufacture of an organic light-emitting device.

Comparative Example 1

An organic light-emitting device was manufactured in the same manner as in Example 1, except that Compound A was used as a dopant instead of Compound 50 in forming the emission layer:

A

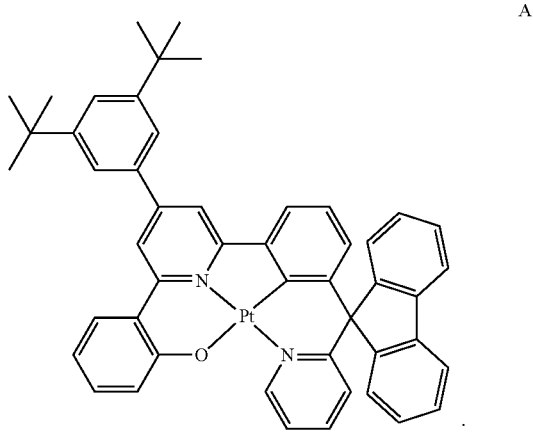

Evaluation Example: Evaluation of Characteristics of the Organic Light-Emitting Devices The driving voltage, current density, brightness, efficiency, emission color, and lifespan ($LT_{97}$) of the organic light-emitting devices of Example 1 and Comparative Example 1 were evaluated. Measuring methods used herein are described below, and results thereof are shown in Table 2:

(1) Measurement of Variation of Current Density According to Voltage Variation

For each of the manufactured organic light-emitting devices, a current value flowing through a unit device was measured with a current-voltage measurement meter (Keithley 2400) by increasing voltage from 0 Volts (V) to 10 V, and the measured current value was divided by area.

(2) Measurement of Variation of Brightness According to Voltage Variation

For each of the manufactured organic light-emitting devices, brightness was measured at each voltage with a brightness meter (Minolta Cs-1000A) by increasing voltage from 0 V to 10 V.

(3) Measurement of Current Efficiency

Based on the current density and the brightness measured in (1) and (2), and a voltage, current efficiency at the same current density (milli Amperes per square centimeter, $mA/cm^2$) was calculated.

(4) Measurement of Lifespan

The time at which the brightness measured in (2) was declined to 97% ($LT_{97}$) was measured for each of the manufactured organic light-emitting devices.

TABLE 2

| | Emission layer | | Driving voltage | Current density | Brightness | Efficiency | Emission color | $LT_{97}$ |
|---|---|---|---|---|---|---|---|---|
| | Host | Dopant | (V) | ($mA/cm^2$) | ($cd/m^2$) | (cd/A) | | (hr) |
| Example 1 | mCP | Compound 50 | 6.5 | 10 | 5,967 | 59.7 | Green | 87 |
| Comparative Example 1 | mCP | Compound A | 8.0 | 10 | 4,035 | 40.4 | Green | 41 |

Referring to Table 2, it was confirmed that the organic light-emitting device of Example 1 had low driving voltage, high luminance, high efficiency, and long lifespan, compared to those of the organic light-emitting device of Comparative Example 1.

An organometallic compound according to embodiments has excellent optical characteristics and electric characteristics and high thermal stability, and an organic light-emitting device including the organometallic compound has high efficiency, long lifespan, and high color purity characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound represented by Formula 1:

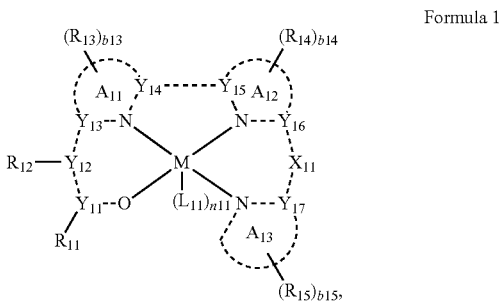

Formula 1 wherein, in Formula 1,

M is selected from a Period I transition metal, a Period II transition metal, and a Period III transition metal, $A_{11}$ to $A_{13}$ are each independently a $C_1$-$C_{20}$ heterocyclic group, $X_{11}$ is selected from $C(R_{16})(R_{17})$ and $C(=O)$, $Y_{11}$ to $Y_{17}$ are each a carbon atom, $Y_{11}$ and O, $Y_{11}$ and $Y_{12}$, $Y_{12}$ and $Y_{13}$, $Y_{13}$ and N, $Y_{14}$ and N, $Y_{14}$ and $Y_{15}$, $Y_{15}$ and N, $Y_{16}$ and N, $Y_{16}$ and $X_{11}$, $Y_{17}$ and $X_{11}$, and $Y_{17}$ and N are each independently connected to each other via a single bond or a double bond, $R_{11}$ to $R_{17}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_1$), —Si($Q_1$)($Q_2$)($Q_3$), —B($Q_1$)($Q_2$), and —N($Q_1$)($Q_2$), wherein two neighboring groups selected from $R_{11}$ to $R_{17}$ are optionally connected to each other to form a condensed ring, wherein $Q_1$ to $Q_3$ are each independently selected from a $C_1$-$C_{60}$ alkyl group and a $C_6$-$C_{60}$ aryl group, b13 to b15 are each independently selected from 1, 2, 3, 4, 5, 6, 7, 8, 9, and 10, $L_{11}$ is selected from a monodentate ligand and a bidentate ligand, and n11 is selected from 0, 1, and 2.

2. The organometallic compound of claim 1, wherein M is selected from Os, Ir, and Pt.

3. The organometallic compound of claim 1, wherein M is Pt.

4. The organometallic compound of claim 1, wherein $A_{11}$ to $A_{13}$ are each independently selected from a pyrrole, an imidazole, a pyrazole, a thiazole, an isothiazole, an oxazole, an isoxazole, an oxadiazole, a triazole, a pyridine, a pyrimidine, a pyrazine, a pyridazine, a triazine, a quinoline, an isoquinoline, a quinoxaline, a quinazoline, an indole, an isoindole, a benzimidazole, a benzoxazole, an isobenzoxazole, and an indazole.

5. The organometallic compound of claim 1, wherein $A_{11}$ to $A_{13}$ are each independently selected from a pyrrole, an imidazole, a pyrazole, a triazole, a pyridine, a pyrimidine, a pyrazine, a pyridazine, a triazine, a quinoline, an isoquinoline, an indole, an isoindole, a benzimidazole, and an indazole.

6. The organometallic compound of claim 1, wherein $A_{11}$ to $A_{13}$ are each independently selected from Formulae 2-1 to 2-6:

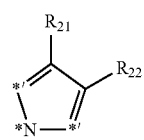
2-1

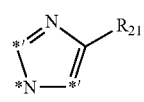
2-2

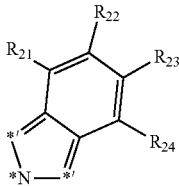
2-3

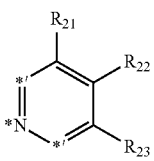
2-4

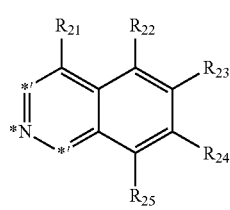
2-5

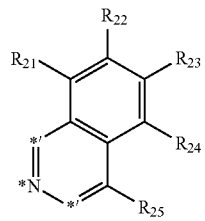
2-6 wherein, in Formula 2-1 to 2-6,

\* indicates a binding site to M in Formula 1,

\*' indicates a binding site to a neighboring atom, $R_{21}$ to $R_{25}$ are each independently the same as described in connection with $R_{11}$ in Formula 1.

7. The organometallic compound of claim 1, wherein $X_{11}$ is $C(R_{16})(R_{17})$, and when $R_{16}$ and $R_{17}$ are connected to each other, $X_{11}$ is represented by one selected from Formulae 3-1 to 3-3:

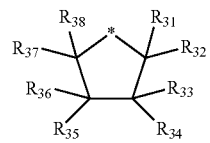
3-1

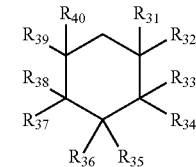
3-2

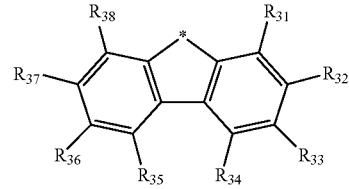
3-3 wherein, in Formulae 3-1 to 3-3,

\* is a carbon atom of $X_{11}$ to which $R_{16}$ and $R_{17}$ are bonded, and $R_{31}$ to $R_{40}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

8. The organometallic compound of claim 7, wherein $R_{31}$ to $R_{40}$ are each independently selected from hydrogen, —F, a cyano group, a methyl group, an iso-propyl group, a tert-butyl group, and —$CF_3$.

9. The organometallic compound of claim 7, wherein $R_{31}$ to $R_{40}$ are hydrogen.

10. The organometallic compound of claim 1, wherein $R_{11}$ to $R_{17}$ are each independently selected from
hydrogen, deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, a tert-butoxy group, a phenyl group, —C(=O)($Q_1$), —Si($Q_1$)($Q_2$)($Q_3$), —B($Q_1$)($Q_2$), and —N($Q_1$)($Q_2$); and
a phenyl group substituted with at least one selected from deuterium, —F, —Cl, —Br, —I, a cyano group, a methyl group, an ethyl group, an n-propyl group, an iso-propyl group, an n-butyl group, an iso-butyl group, a sec-butyl group, a tert-butyl group, —$CF_3$, a methoxy group, an ethoxy group, and a tert-butoxy group,
wherein $Q_1$ to $Q_3$ are each independently selected from a methyl group, an ethyl group, an n-propyl group, an iso-propyl group, an n-butyl group, an iso-butyl group, a sec-butyl group, a tert-butyl group, and a phenyl group.

11. The organometallic compound of claim 1, wherein $R_{11}$ to $R_{17}$ are each independently selected from
hydrogen, deuterium, —F, a cyano group, a methyl group, an ethyl group, an n-propyl group, an iso-propyl group, an n-butyl group, an iso-butyl group, a sec-butyl group, a tert-butyl group, —$CF_3$, —C(=O)($Q_1$), —Si($Q_1$)($Q_2$)($Q_3$), —B($Q_1$)($Q_2$), and —N($Q_1$)($Q_2$); and
a phenyl group substituted with at least one selected from deuterium, —F, a cyano group, a methyl group, an ethyl group, an n-propyl group, an iso-propyl group, an n-butyl group, an iso-butyl group, a sec-butyl group, a tert-butyl group, and —$CF_3$,
wherein $Q_1$ to $Q_3$ are each independently selected from a methyl group, an ethyl group, an n-propyl group, an iso-propyl group, an n-butyl group, an iso-butyl group, a sec-butyl group, a tert-butyl group, and a phenyl group.

12. The organometallic compound of claim 1, wherein $R_{11}$ to $R_{17}$ are each independently selected from hydrogen, —F, a cyano group, a methyl group, an ethyl group, an iso-propyl group, a tert-butyl group, —$CF_3$, —Si($CH_3$)$_3$, and groups represented by Formulae 5-1 and 5-2:

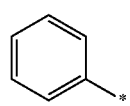

5-1

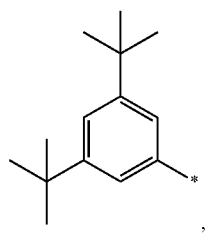

5-2 wherein, in Formula 5-1 and 5-2,

* indicates a binding site to a neighboring atom.

13. The organometallic compound of claim 1, wherein the organometallic compound is represented by one selected from Formulae 1-1 to 1-6:

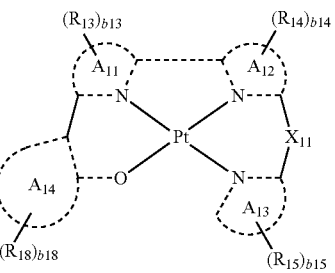

1-1

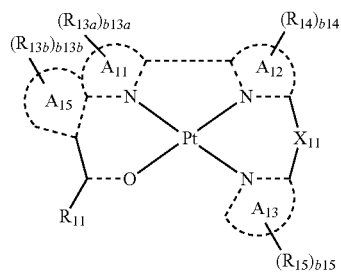

1-2

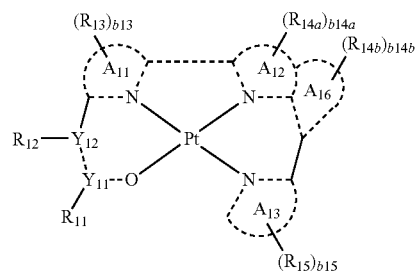

1-3

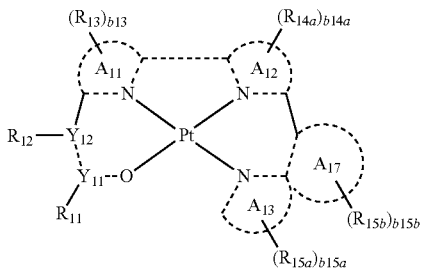

1-4 wherein, in Formulae 1-1 to 1-6, $A_{11}$ to $A_{13}$, $X_{11}$, $Y_{11}$, $Y_{12}$, $R_{11}$ to $R_{15}$, and b13 to b15 are the same as in Formula 1, $R_{13a}$ and $R_{13b}$ are each independently the same as $R_{13}$ in Formula 1, $R_{14a}$ and $R_{14b}$ are each independently the same as $R_{14}$ in Formula 1, $R_{15a}$ and $R_{15b}$ are each independently the same as $R_{15}$ in Formula 1, $R_{18}$ is the same as $R_{11}$ in Formula 1, b13a and b13b are each independently the same as b13 in Formula 1, b14a and b14b are each independently the same as b14 in Formula 1, b15a and b15b are each independently the same as b15 in Formula 1, b18 is the same as b11 in Formula 1, and $A_{14}$ to $A_{17}$ are each independently selected from a $C_5$-$C_{20}$ carbocyclic group and a $C_1$-$C_{20}$ heterocyclic group.

14. The organometallic compound of claim 13, wherein $A_{14}$ to $A_{17}$ are each independently selected from a benzene, a naphthalene, a fluorene, an indene, a furan, a thiophene, a carbazole, a benzofuran, a benzothiophene, a dibenzofuran, and a dibenzothiophene.

15. The organometallic compound of claim 1, wherein the organometallic compound is represented by one selected from Formulae 1-11 to 1-19 and 1-5:

1-15
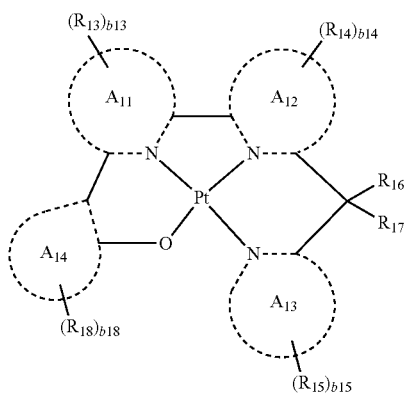

1-16
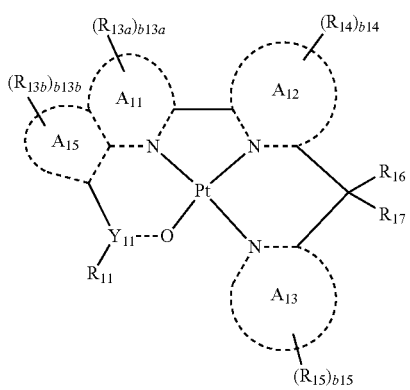

1-17
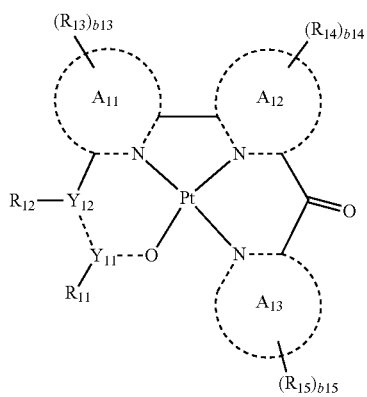

1-18
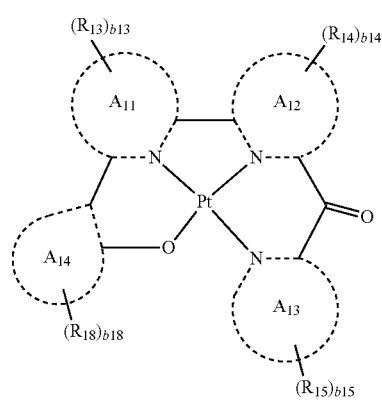

1-19
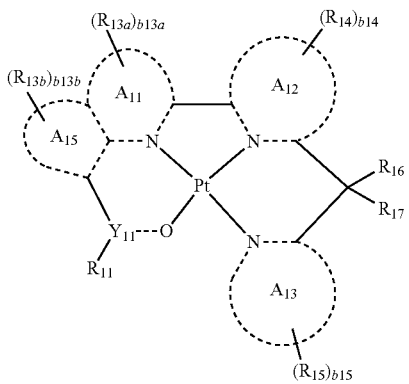

1-5
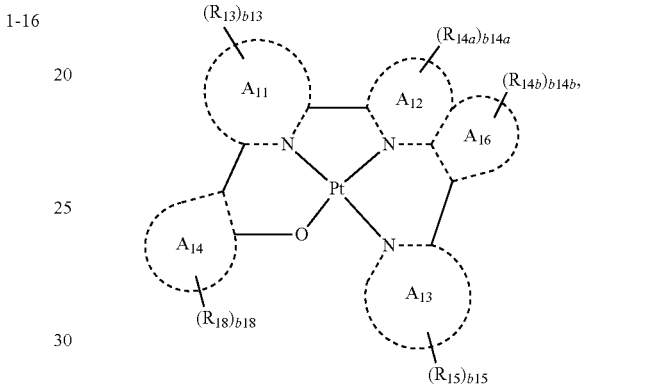

wherein, in Formulae 1-11 to 1-19 and 1-5,
$A_{11}$ to $A_{13}$, $Y_{11}$, $Y_{12}$, $R_{11}$ to $R_{17}$, and b13 to b15 are the same as in Formula 1,
$R_{13a}$ and $R_{13b}$ are each independently the same as $R_{13}$ in Formula 1,
$R_{14a}$ and $R_{14b}$ are each independently the same as $R_{14}$ in Formula 1,
$R_{18}$ is the same as $R_{11}$ in Formula 1,
b13a and b13b are each independently the same as b13 in Formula 1,
14a and b14b are each independently the same as b14 in Formula 1,
b18 is the same as b11 in Formula 1,
$A_{14}$ to $A_{16}$ are each independently selected from a $C_5$-$C_{20}$ carbocyclic group and a $C_1$-$C_{20}$ heterocyclic group, and
$R_{31}$ to $R_{38}$ are each independently selected from
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

16. The organometallic compound of claim 15, wherein $A_{11}$ to $A_{13}$ are each independently selected from a pyrrole, an imidazole, a pyrazole, a triazole, a pyridine, a pyrimidine, a pyrazine, a pyridazine, a triazine, a quinoline, an isoquinoline, an indole, an isoindole, a benzimidazole, and an indazole, and $A_{14}$ to $A_{16}$ are each independently selected from a benzene, a naphthalene, a fluorene, an indene, a furan, a thiophene, a carbazole, a benzofuran, a benzothiophene, a dibenzofuran, and a dibenzothiophene.

17. The organometallic compound of claim 1, wherein the organometallic compound is selected from Compounds 1 to 50:

1
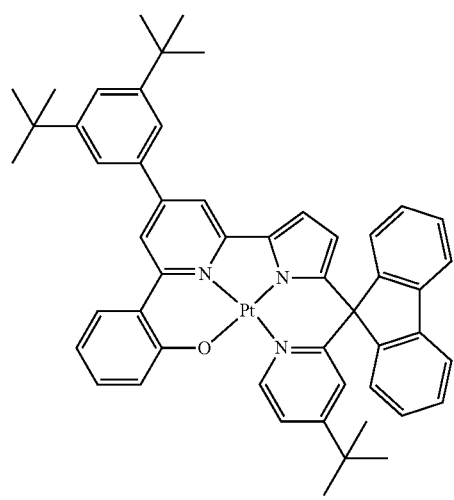

2
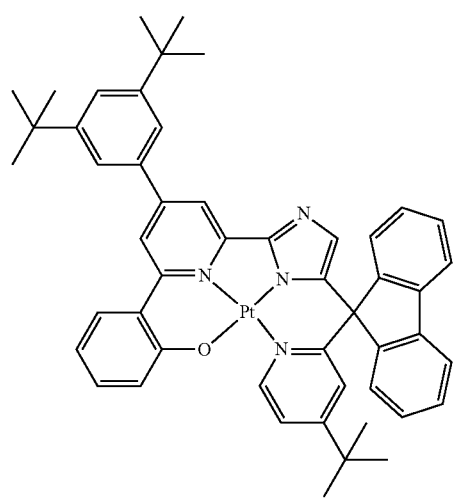

3
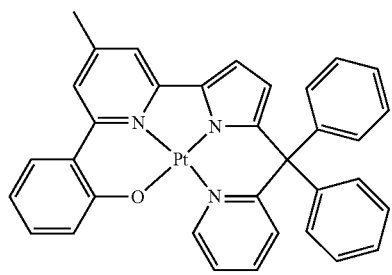

4
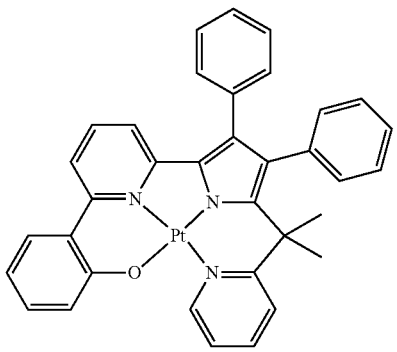

5
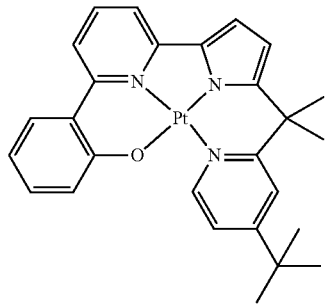

6
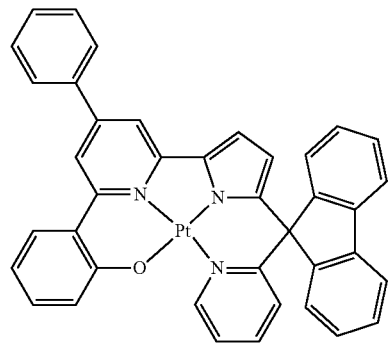

7
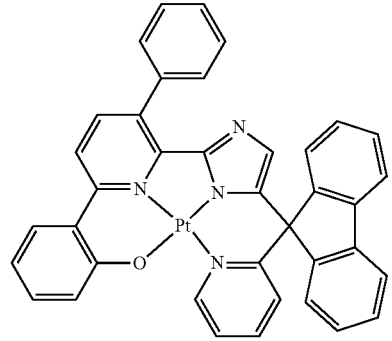

8
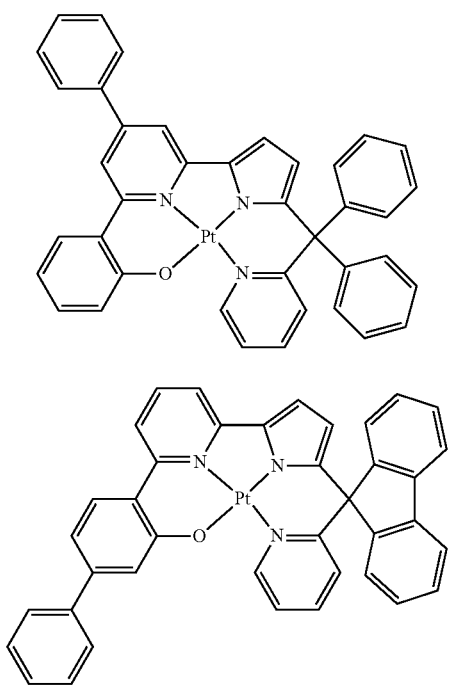
9
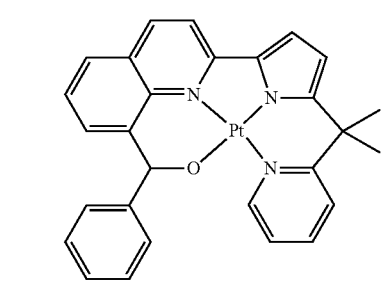
10
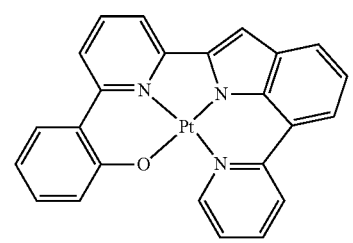
11
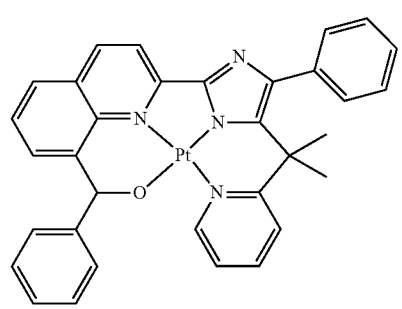
12
13
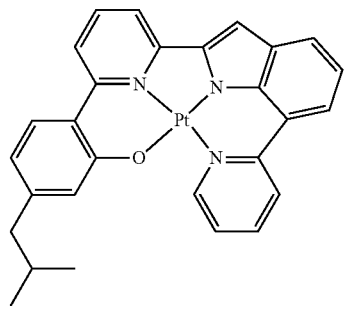
14
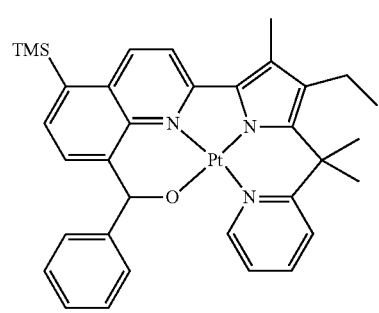
15
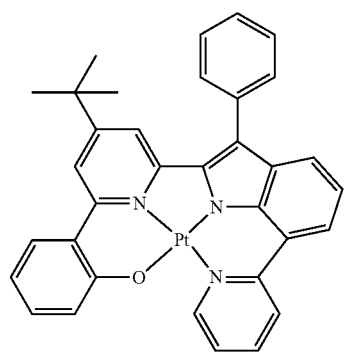
16
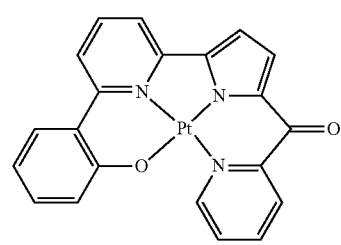
17
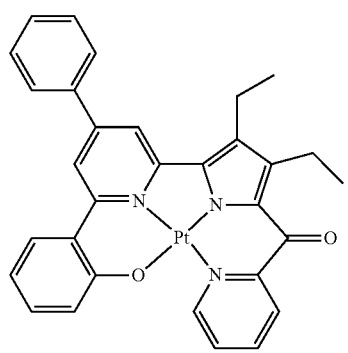

18
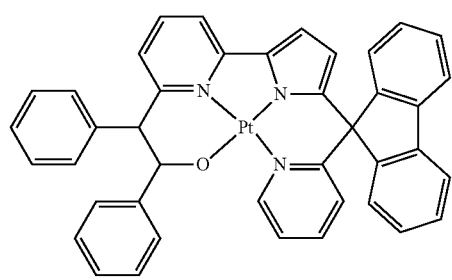
19
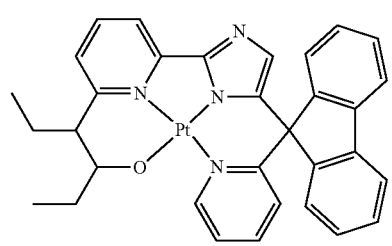
20
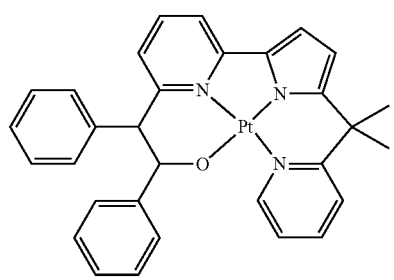
21
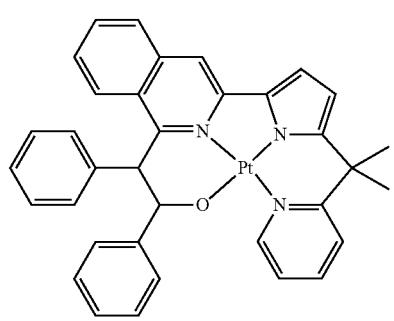
22
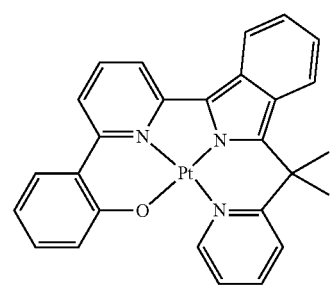
23
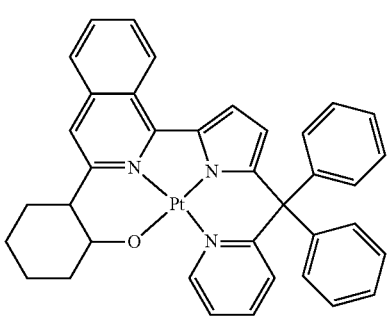
24
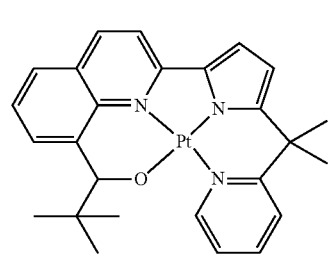
25
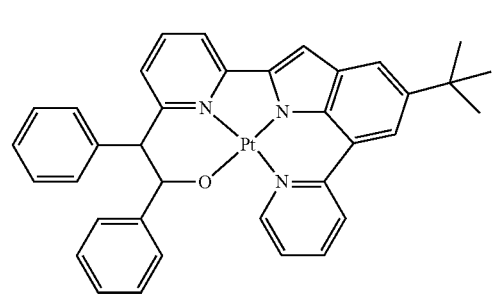
26
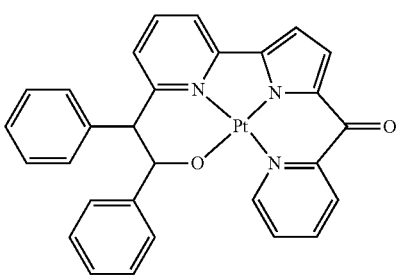
27
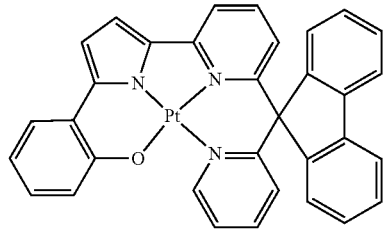
28
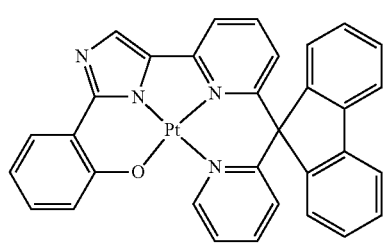

29
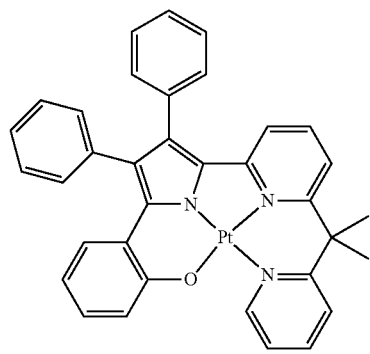
30
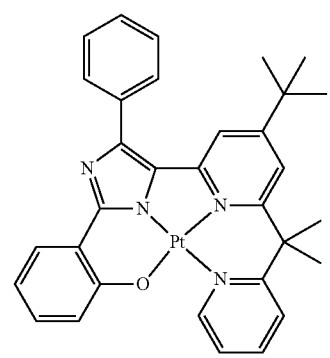
31
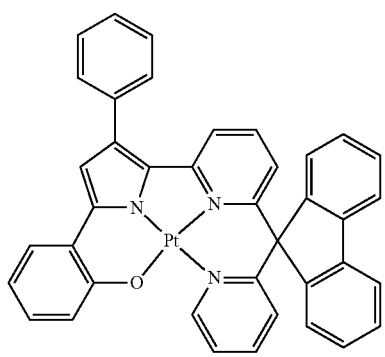
32
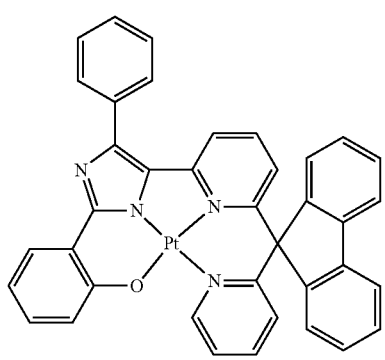
33
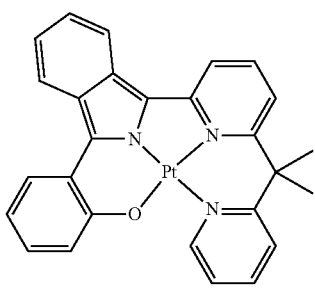
34
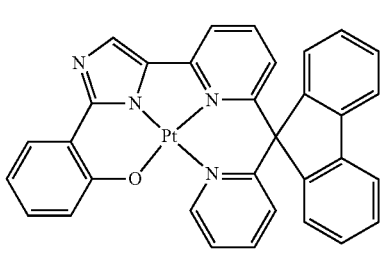
35
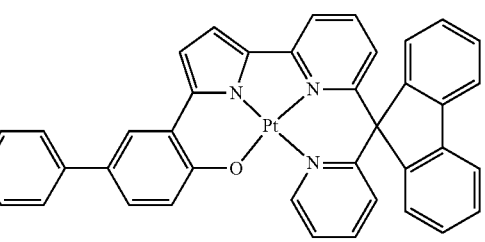
36
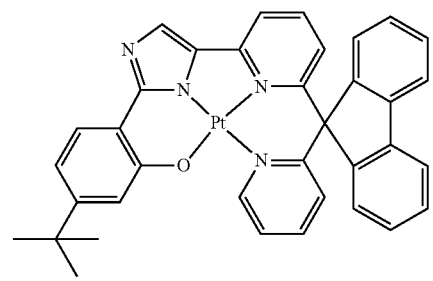
37
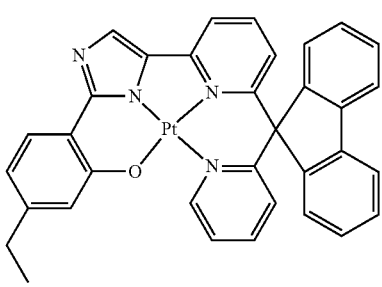

-continued
38
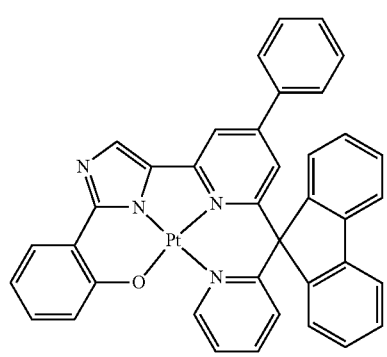
39
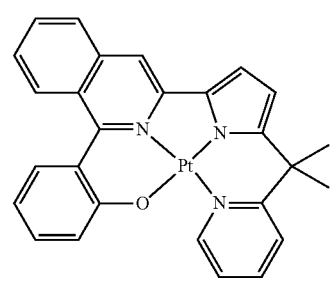
40
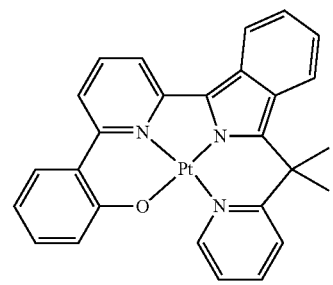
41
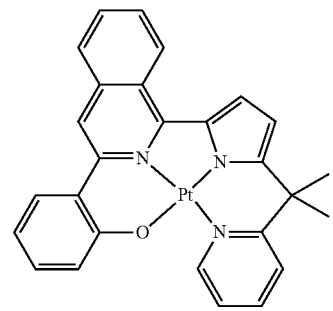
42
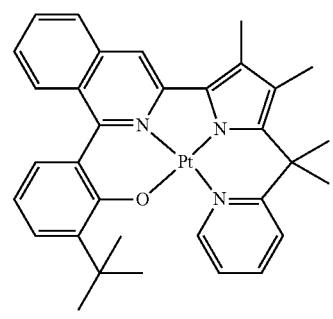
-continued
43
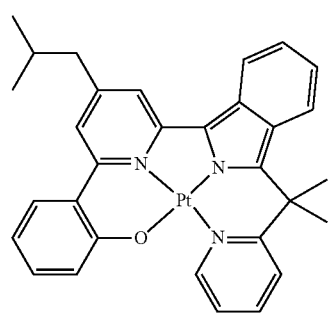
44
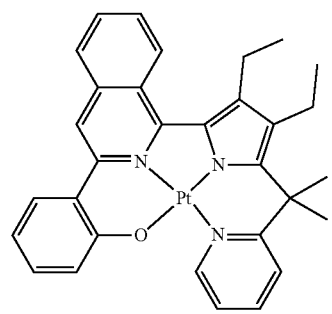
45
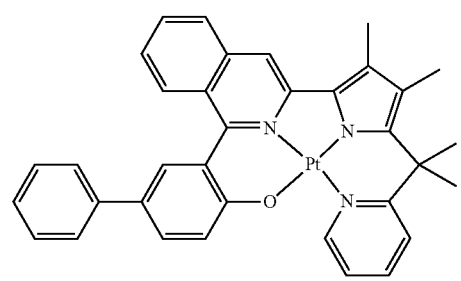
46
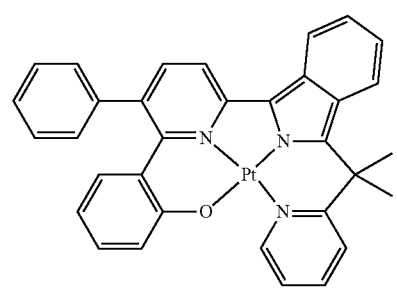
47
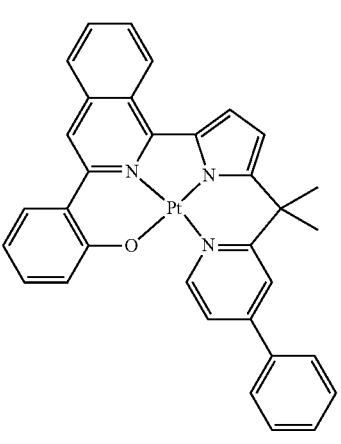

-continued

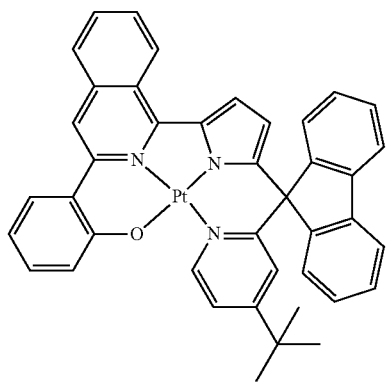
48

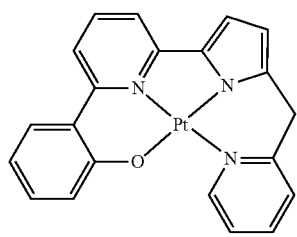
49

-continued

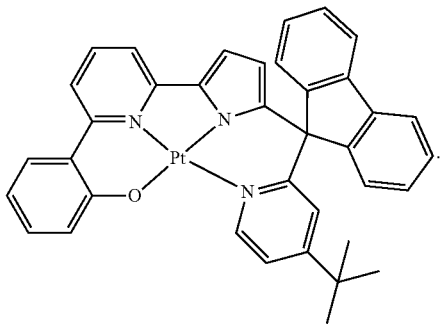
50

18. An organic light-emitting device comprising:
   a first electrode;
   a second electrode; and
   an organic layer disposed between the first electrode and the second electrode, wherein the organic layer comprises an emission layer and at least one organometallic compound of claim 1.

19. The organic light-emitting device of claim 18, wherein the emission layer comprises the organometallic compound.

20. The organic light-emitting device of claim 19, wherein the emission layer further comprises a host, and wherein the organometallic compound is a dopant.

* * * * *